United States Patent
Sekiya et al.

(10) Patent No.: US 12,416,601 B2
(45) Date of Patent: Sep. 16, 2025

(54) GAS SENSOR

(71) Applicant: NGK INSULATORS, LTD., Aichi (JP)

(72) Inventors: Takayuki Sekiya, Nissin (JP); Yusuke Watanabe, Nagoya (JP)

(73) Assignee: NGK INSULATORS, LTD., Nagoya (JP)

( * ) Notice: Subject to any disclaimer, the term of this patent is extended or adjusted under 35 U.S.C. 154(b) by 671 days.

(21) Appl. No.: 17/483,657

(22) Filed: Sep. 23, 2021

(65) Prior Publication Data

US 2022/0011261 A1 Jan. 13, 2022

Related U.S. Application Data

(63) Continuation of application No. PCT/JP2020/013415, filed on Mar. 25, 2020.

(30) Foreign Application Priority Data

Mar. 28, 2019 (JP) .................. 2019-064322

(51) Int. Cl.
  *G01N 27/41* (2006.01)
  *G01N 27/30* (2006.01)
  (Continued)

(52) U.S. Cl.
  CPC ........... *G01N 27/41* (2013.01); *G01N 27/301* (2013.01); *G01N 27/4071* (2013.01); *G01N 27/4075* (2013.01); *G01N 33/0037* (2013.01)

(58) Field of Classification Search
  CPC .. G01N 27/41; G01N 27/301; G01N 27/4071; G01N 27/4075; G01N 33/0037; G01N 27/419; Y02A 50/20
  See application file for complete search history.

(56) References Cited

U.S. PATENT DOCUMENTS 11,054,388 B2 * 7/2021 Koyabu ............. G01N 27/4175
2004/0089544 A1 5/2004 Kato et al.
(Continued)

FOREIGN PATENT DOCUMENTS

| | | |
|---|---|---|
| CN | 108693236 A | 10/2018 |
| JP | 11-183436 A | 7/1999 |

(Continued)

OTHER PUBLICATIONS

Ieda et al., English translation of JP-2010071898-A, 2010.*

(Continued)

*Primary Examiner* — James Lin
*Assistant Examiner* — Sommer Yousef Osman
(74) *Attorney, Agent, or Firm* — MATTINGLY & MALUR, PC

(57) ABSTRACT

A gas sensor detects a specific gas concentration in a measurement-object gas and includes an element body and one or more pump cells. The element body includes an oxygen-ion-conductive solid electrolyte layer and is provided with a measurement-object gas flow section therein. The measurement-object gas flow section receives a measurement-object gas and allows the measurement-object gas to flow therethrough. The one or more pump cells each have an inner electrode and an outer pump electrode and pump out oxygen from around the inner electrode to around the outer pump electrode. The inner electrode is disposed in the measurement-object gas flow section and contains a catalytically-active noble metal. At least one pump cell of the one or more pump cells pumps out the oxygen by applying a repeatedly on-off controlled pump current between a measurement electrode and the outer pump electrode.

2 Claims, 7 Drawing Sheets

(51) Int. Cl.
*G01N 27/407* (2006.01)
*G01N 33/00* (2006.01)

(56) References Cited

U.S. PATENT DOCUMENTS

| | | | |
|---|---|---|---|
| 2005/0173264 A1* | 8/2005 | Reitmeier | G01N 27/419 205/783.5 |
| 2007/0034531 A1 | 2/2007 | Kato et al. | |
| 2007/0261475 A1* | 11/2007 | Allmendinger | G01N 27/419 73/31.05 |
| 2008/0237064 A1* | 10/2008 | Nakasone | G01N 27/4175 205/781 |
| 2012/0097553 A1 | 4/2012 | Classen | |
| 2015/0268192 A1* | 9/2015 | Saito | G01N 27/419 205/793 |
| 2015/0276657 A1 | 10/2015 | Sekiya et al. | |
| 2015/0276659 A1* | 10/2015 | Sekiya | G01N 27/4071 204/416 |
| 2017/0219517 A1* | 8/2017 | Uematsu | G01N 27/41 |
| 2018/0074009 A1* | 3/2018 | Okamoto | G01N 33/0054 |
| 2018/0231492 A1* | 8/2018 | Aoki | G01N 27/4067 |
| 2018/0284052 A1 | 10/2018 | Watanabe et al. | |

FOREIGN PATENT DOCUMENTS

| | | | | |
|---|---|---|---|---|
| JP | 3860896 B2 * | 12/2006 | | G01N 27/419 |
| JP | 2010071898 A * | 4/2010 | | |
| JP | 2015-200642 A | 11/2015 | | |
| JP | 2018-173319 A | 11/2018 | | |

OTHER PUBLICATIONS

Schneider et al., "Microcontrollers vs.microprocessors: What's the difference?", 2024, IBM Blog, pp. 2-10, https://www.ibm.com/blog/microcontroller-vs-microprocessor/ (Year: 2024).*
International Preliminary Report on Patentability received in corresponding International Application No. PCT/JP2020/013415 dated Oct. 7, 2021.
International Search Report of PCT/JP2020/013415 dated Jun. 30, 2020.
Chinese Office Action received in corresponding Chinese Application No. 202080023087.8 dated Oct. 12, 2023.

* cited by examiner

GAS SENSOR

CROSS-REFERENCE TO RELATED APPLICATION

This application is a continuation application of PCT/JP2020/013415, filed on Mar. 25, 2020, which claims the benefit of priority of Japanese Patent Application No. 2019-064322, filed on Mar. 28, 2019, the entire contents of which are incorporated herein by reference.

BACKGROUND OF THE INVENTION

1. Field of the Invention

The present invention relates to gas sensors.

2. Description of the Related Art

A known gas sensor in the related art detects the concentration of a specific gas, such as NOx, in a measurement-object gas, such as exhaust gas of an automobile. For example, Patent Literature 1 describes a gas sensor including a layered body of a plurality of oxygen-ion-conductive solid electrolyte layers, a main pump cell, and a measurement pump cell. The main pump cell includes an inner pump electrode disposed in a measurement-object gas flow section inside the layered body, and also includes an outer pump electrode disposed outside the layered body. The measurement pump cell includes a measurement electrode disposed in the measurement-object gas flow section, and also includes an outer pump electrode. When this gas sensor is to detect the NOx concentration, the main pump cell first pumps out oxygen from the measurement-object gas flow section or pumps oxygen into the measurement-object gas flow section, so that the oxygen concentration in the measurement-object gas flow section is adjusted. Subsequently, after the oxygen concentration is adjusted, NOx in the measurement-object gas is reduced, and oxygen produced as a result of the reduction is pumped out by the measurement pump cell. Based on a pump current flowing through the measurement pump cell, the NOx concentration in the measurement-object gas is detected.

CITATION LIST

Patent Literature

PTL 1: JP 2015-200642 A

SUMMARY OF THE INVENTION

Each of the electrodes included in the pump cells of the gas sensor is catalytically active (i.e., has catalytic performance) and serves as a catalyst for a reaction where oxygen turns into ions. However, as the gas sensor is used, the catalytic activity of this electrode may change, as in a case where the catalytic activity decreases (i.e., is deactivated). A change in the catalytic activity may sometimes lead to a problem in the gas sensor, such as deterioration in the sensitivity for detecting the specific gas concentration.

The present invention has been made to solve such a problem, and a main object thereof is to suppress a change in the catalytic activity of an electrode due to use of the gas sensor.

The present invention provides the following solutions for achieving the main object mentioned above.

A gas sensor according to the present invention detects a specific gas concentration in a measurement-object gas and includes an element body and one or more pump cells. The element body includes an oxygen-ion-conductive solid electrolyte layer and is provided with a measurement-object gas flow section therein. The measurement-object gas flow section receives a measurement-object gas and allows the measurement-object gas to flow therethrough. The one or more pump cells each have an inner electrode and an outer electrode and pump out oxygen from around the inner electrode to around the outer electrode. The inner electrode is disposed in the measurement-object gas flow section and contains a catalytically-active noble metal. The outer electrode is disposed in an area to be exposed to the measurement-object gas at an outer side of the element body. At least one pump cell of the one or more pump cells pumps out the oxygen by applying a repeatedly on-off controlled pump current between the inner electrode and the outer electrode.

This gas sensor includes the one or more pump cells. At least one of the pump cells pumps out the oxygen from around the inner electrode to around the outer electrode by applying the repeatedly on-off controlled pump current between the inner electrode and the outer electrode. By applying the repeatedly on-off controlled pump current (referred to as "intermittent pump current" hereinafter) in this manner, a change in the catalytic activity of the inner electrode due to use of the gas sensor can be suppressed, as compared with a case where a continuous pump current is applied to a pump cell. A conceivable reason for this will be described below. When oxygen is to be pumped out from around the inner electrode by applying the pump current between the inner electrode and the outer electrode, the surrounding oxygen turns into oxygen ions inside the inner electrode. The oxygen ions serve as electron carriers and travel toward the outer electrode. During this process, if the pump current is a continuous electric current, a reaction where some noble metals in the inner electrode oxidize and a reaction where oxygen ions are released as a result of reduction of the oxidized noble metals both occur. When both reactions reach a state of equilibrium, some of the noble metals in the inner electrode are in a constantly oxidized state. Since oxidized noble metals tend to evaporate more easily than before they are oxidized, the noble metals in the inner electrode tend to decrease with use of the gas sensor, thus causing the catalytic activity of the inner electrode to change. On the other hand, the following description relates to a case where an intermittent pump current is used and is intermittently applied such that the intermittent pump current becomes an average electric current equal to the continuous pump current. In this case, the pump current applied to the inner electrode during an on mode is a value larger than the continuous pump current. Accordingly, the oxygen inside the inner electrode turns into ions and travel toward the outer electrode more during the on mode of the intermittent pump current than when the pump current is applied continuously, so that the oxygen concentration inside the inner electrode decreases. In such a state where the oxygen concentration inside the inner electrode is low, the aforementioned noble metals in the inner electrode are less likely to oxidize, and rather, reduction of oxidized noble metals may occur. Thus, a decrease in the aforementioned noble metals in the inner electrode with use of the gas sensor is suppressed. Furthermore, electric current hardly flows to the inner electrode when the pump current is in an off mode, so that oxidization of the aforementioned noble metals in the inner electrode is less likely to occur. As a result, oxidization of the noble metals in the inner electrode is suppressed in both an on mode and an off mode. It is thus conceivable that a change in the catalytic activity of the inner electrode due to use of the gas sensor is suppressed.

In the gas sensor according to the present invention, the one or more pump cells may include a main pump cell, an auxiliary pump cell, and a measurement pump cell. The main pump cell has an inner main pump electrode serving as the inner electrode and an outer main pump electrode serving as the outer electrode. The inner main pump electrode is disposed in a first internal cavity in the measurement-object gas flow section. The main pump cell pumps out oxygen from the first internal cavity. The auxiliary pump cell has an inner auxiliary pump electrode serving as the inner electrode and an outer auxiliary pump electrode serving as the outer electrode. The inner auxiliary pump electrode is disposed in a second internal cavity provided downstream of the first internal cavity in the measurement-object gas flow section. The auxiliary pump cell pumps out oxygen from the second internal cavity. The measurement pump cell has an inner measurement electrode serving as the inner electrode and an outer measurement electrode serving as the outer electrode. The inner measurement electrode is disposed in a measurement chamber provided downstream of the second internal cavity in the measurement-object gas flow section. The measurement pump cell pumps out oxygen produced in the measurement chamber from the specific gas. At least one of the main pump cell, the auxiliary pump cell, and the measurement pump cell pumps out the oxygen from around the inner electrode by applying the repeatedly on-off controlled pump current between the inner electrode and the outer electrode. Accordingly, with regard to a pump cell that is caused to operate by receiving an intermittent pump current among the main pump cell, the auxiliary pump cell, and the measurement pump cell, a change in the catalytic activity of the inner electrode due to use of the gas sensor can be suppressed.

In this case, the measurement pump cell may pump out the oxygen by applying a measurement pump current serving as the repeatedly on-off controlled pump current between the inner measurement electrode and the outer measurement electrode. In other words, among the main pump cell, the auxiliary pump cell, and the measurement pump cell, at least the measurement pump cell may be caused to operate by using an intermittent pump current. Accordingly, a change in the catalytic activity of the inner measurement electrode due to use of the gas sensor can be suppressed. A change in the catalytic activity of the inner measurement electrode has a greater effect on the sensitivity for detecting the specific gas concentration in the gas sensor than a change in the catalytic activity of the inner main pump electrode and the inner auxiliary pump electrode. Therefore, deterioration in the detection sensitivity may be readily minimized by suppressing a change in the catalytic activity of the inner measurement electrode.

In this case, the gas sensor according to the present invention may further include a reference electrode, a measurement-voltage detection device, a measurement-pump-cell control device, and a specific-gas-concentration detection device. The reference electrode is disposed inside the element body and receives a reference gas serving as a reference for detection of the specific gas concentration. The measurement-voltage detection device detects a measurement voltage between the reference electrode and the inner measurement electrode. The measurement-pump-cell control device controls the measurement pump current based on the measurement voltage during a second period so as to set an oxygen concentration in the measurement chamber to a predetermined low concentration. The second period is one of a first period in which a change has occurred in the measurement voltage due to the measurement pump current being in an on mode and a second period in which the change in the measurement voltage has receded as compared with the first period due to the measurement pump current being in an off mode. The specific-gas-concentration detection device detects the specific gas concentration in the measurement-object gas based on the measurement pump current. The effect that the measurement pump current has on the measurement voltage during the second period is smaller than during the first period. Therefore, the oxygen concentration in the measurement chamber is adjusted by controlling the measurement pump current based on the measurement voltage during the second period, and the specific gas concentration in the measurement-object gas is detected based on the measurement pump current, whereby the specific gas concentration can be accurately detected.

In the example where the measurement pump cell pumps out the oxygen by applying the repeatedly on-off controlled measurement pump current, the gas sensor according to the present invention may further include a reference electrode, a measurement-voltage detection device, a measurement-pump-cell control device, and a specific-gas-concentration detection device. The reference electrode is disposed inside the element body and receives a reference gas serving as a reference for detection of the specific gas concentration. The measurement-voltage detection device detects a measurement voltage between the reference electrode and the inner measurement electrode. The measurement-pump-cell control device controls the measurement pump current so as to set an average value of the measurement pump current to a predetermined target value. The specific-gas-concentration detection device detects the specific gas concentration in the measurement-object gas based on the measurement voltage during a second period. The second period is one of a first period in which a change has occurred in the measurement voltage due to the measurement pump current being in an on mode and a second period in which the change in the measurement voltage has receded as compared with the first period due to the measurement pump current being in an off mode. Accordingly, the specific gas concentration in the measurement-object gas can be detected. Moreover, the specific gas concentration in the measurement-object gas is detected based on the measurement voltage during the second period, whereby the specific gas concentration can be accurately detected.

DETAILED DESCRIPTION OF THE INVENTION

Figure 1:
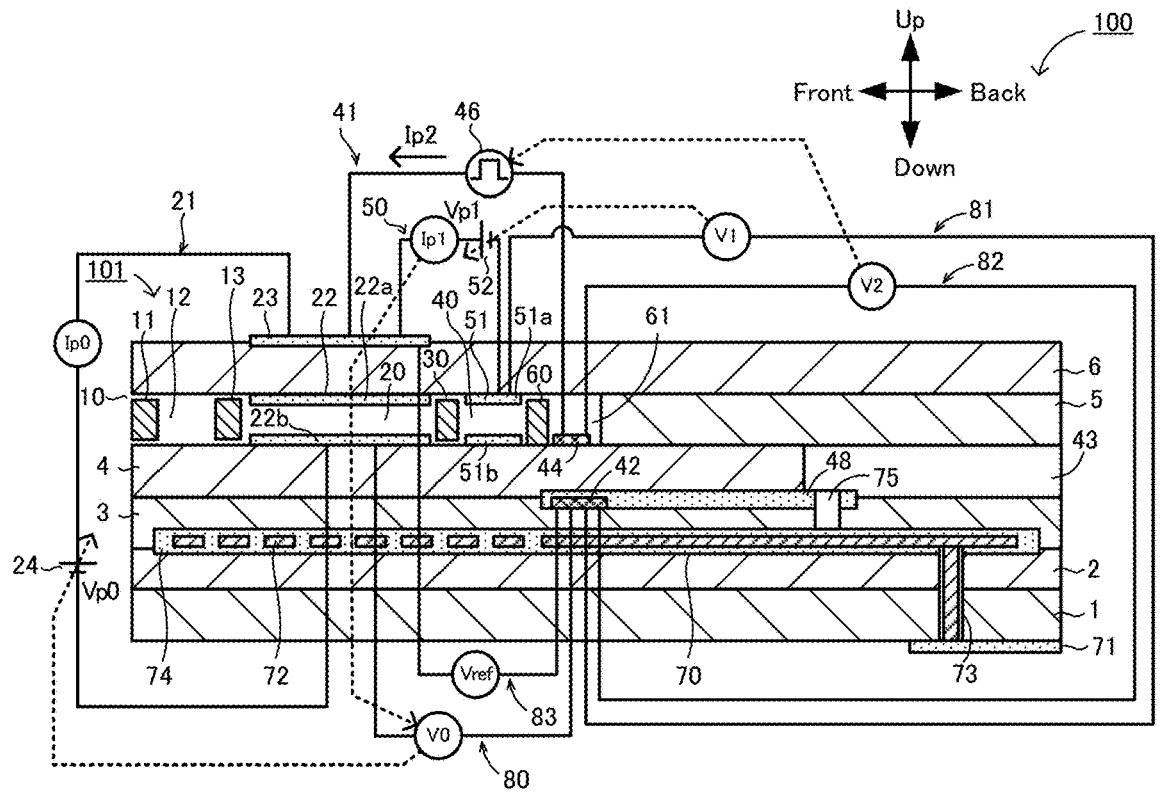
FIG. 1 is a schematic cross-sectional view of a gas sensor 100.
Figure 2:
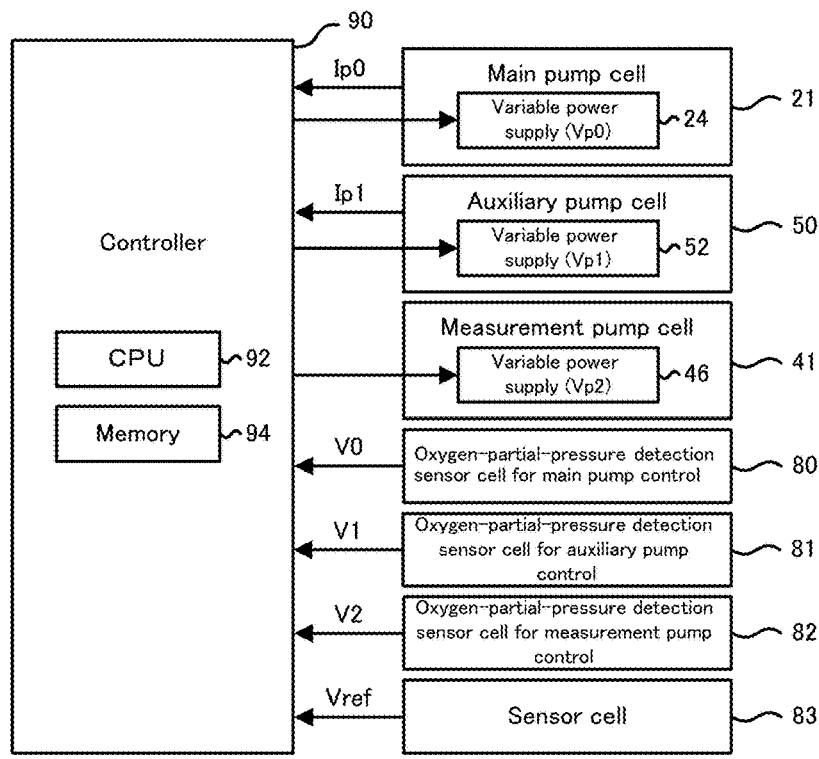
FIG. 2 is a block diagram illustrating an electrical connection relationship between a controller 90 and individual cells.

Embodiments of the present invention will now be described with reference to the drawings. FIG. 1 is a schematic cross-sectional view schematically illustrating an example of the configuration of a gas sensor 100 according to an embodiment of the present invention. FIG. 2 is a block diagram illustrating an electrical connection relationship between a controller 90 and individual cells. This gas sensor 100 is attached to a pipe, such as an exhaust gas pipe of an internal combustion engine. The gas sensor 100 detects the concentration of a specific gas, such as NOx or ammonia, in a measurement-object gas, such as exhaust gas of the internal combustion engine. In this embodiment, the gas sensor 100 measures the $NO_x$ concentration as the specific gas concentration. The gas sensor 100 includes a sensor element 101 having an elongated rectangular parallelepiped shape, individual cells 21, 41, 50, and 80 to 83 each including a part of the sensor element 101, and the controller 90 that controls the entire gas sensor 100.

The sensor element 101 is an element including a layered body in which six layers, namely a first substrate layer 1, a second substrate layer 2, a third substrate layer 3, a first solid electrolyte layer 4, a spacer layer 5, and a second solid electrolyte layer 6, are layered in this order from the bottom side, as viewed in the drawing. Each of the six layers is formed of an oxygen-ion-conductive solid electrolyte layer containing, for example, zirconia ($ZrO2$). The solid electrolyte forming these six layers is dense and gastight. This sensor element 101 is manufactured, for example, by stacking ceramic green sheets corresponding to the individual layers on top of each other, for example, after predetermined processing and circuit pattern printing, and then firing the stacked ceramic green sheets so that they are combined together.

A gas inlet 10, a first diffusion control section 11, a buffer space 12, a second diffusion control section 13, a first internal cavity 20, a third diffusion control section 30, a second internal cavity 40, a fourth diffusion control section 60, and a third internal cavity 61 are formed adjacent to each other so as to communicate in the above order between the lower surface of the second solid electrolyte layer 6 and the upper surface of the first solid electrolyte layer 4 on the front end side (on the left end side in FIG. 1) of the sensor element 101.

The gas inlet 10, the buffer space 12, the first internal space 20, the second internal space 40, and the third internal space 61 constitute a space within the sensor element 101. The space is provided in such a manner that a portion of the spacer layer 5 is hollowed out. The top of the space is defined by the lower surface of the second solid electrolyte layer 6, the bottom of the space is defined by the upper surface of the first solid electrolyte layer 4, and sides of the space are defined by side surfaces of the spacer layer 5.

The first diffusion control section 11, the second diffusion control section 13, and the third diffusion control section 30 are each provided as two laterally elongated slits (i.e., the longitudinal direction of the openings is perpendicular to the figure). The fourth diffusion control section 60 is provided as a single laterally elongated slit (i.e., the longitudinal direction of the opening is perpendicular to the figure) formed as a clearance under the lower surface of the second solid electrolyte layer 6. The section extending from the gas inlet 10 to the third internal cavity 61 is also referred to as "measurement-object gas flow section".

A reference gas introduction space 43 is disposed between the upper surface of the third substrate layer 3 and the lower surface of the spacer layer 5 at a position farther away from the front end side than the measurement-object gas flow section. The reference gas introduction space 43 is defined at both sides by the side surfaces of the first solid electrolyte layer 4. As an example of a reference gas for NOx concentration measurement, air is introduced into the reference gas introduction space 43.

An air introduction layer 48 is a porous ceramic layer. The reference gas is introduced into the air introduction layer 48 through the reference gas introduction space 43. The air introduction layer 48 is formed so as to cover a reference electrode 42.

The reference electrode 42 is formed between the upper surface of the third substrate layer 3 and the first solid electrolyte layer 4. As described above, the air introduction layer 48 leading to the reference gas introduction space 43 is disposed around the reference electrode 42. As described later, the reference electrode 42 can be used to measure the oxygen concentrations (oxygen partial pressures) in the first internal cavity 20, the second internal cavity 40, and the third internal cavity 61. The reference electrode 42 is formed as a porous cermet electrode (e.g., a cermet electrode composed of Pt and $ZrO_2$).

The gas inlet 10 of the measurement-object gas flow section is exposed to the external space. The measurement-object gas is taken into the sensor element 101 through the gas inlet 10 from the external space. The first diffusion control section 11 applies a predetermined diffusion resistance to the measurement-object gas taken in through the gas inlet 10. The buffer space 12 is provided for guiding the measurement-object gas introduced by the first diffusion control section 11 to the second diffusion control section 13. The second diffusion control section 13 applies a predetermined diffusion resistance to the measurement-object gas introduced to the first internal cavity 20 from the buffer space 12. When the measurement-object gas is to be introduced to the first internal cavity 20 from outside the sensor element 101, the measurement-object gas quickly taken into the sensor element 101 through the gas inlet 10 due to pressure fluctuations of the measurement-object gas in the external space (i.e., pulsations of exhaust pressure if the measurement-object gas is exhaust gas of an automobile) is not directly introduced to the first internal cavity 20 but is introduced to the first internal cavity 20 after the pressure fluctuations of the measurement-object gas are negated through the first diffusion control section 11, the buffer space 12, and the second diffusion control section 13. Accordingly, the pressure fluctuations of the measurement-object gas to be introduced to the first internal cavity 20 can be made substantially negligible. The first internal cavity 20 is provided as a space for adjusting the oxygen partial pressure in the measurement-object gas introduced via the second diffusion control section 13. The oxygen partial pressure is adjusted by actuating a main pump cell 21.

The main pump cell 21 is an electrochemical pump cell composed of an inner pump electrode 22 having a ceiling electrode portion 22a disposed over substantially an entire portion of the lower surface of the second solid electrolyte layer 6 that faces the first internal cavity 20, an outer pump electrode 23 disposed on a region of the upper surface of the second solid electrolyte layer 6 that corresponds to the ceiling electrode portion 22a so as to be exposed to the external space, and a portion of the second solid electrolyte layer 6 that is located between the inner pump electrode 22 and the outer pump electrode 23.

The inner pump electrode 22 is formed on portions of the upper and lower solid electrolyte layers (the second solid electrolyte layer 6 and the first solid electrolyte layer 4) that define the first internal cavity 20 and portions of the spacer layer 5 that give the sidewalls of the first internal cavity 20. Specifically, the ceiling electrode portion 22a is formed on a portion of the lower surface of the second solid electrolyte layer 6 that gives the ceiling surface of the first internal cavity 20. A bottom electrode portion 22b is formed on a portion of the upper surface of the first solid electrolyte layer 4 that gives the bottom surface of the first internal cavity 20. Side electrode portions (not shown) are formed on portions of the sidewall surfaces (inner surfaces) of the spacer layer 5 that form both sidewalls of the first internal cavity 20 so as to join together the ceiling electrode portion 22a and the bottom electrode portion 22b. Thus, the inner pump electrode 22 is provided as a tunnel-like structure in the area where the side electrode portions are disposed.

The inner pump electrode 22 contains a catalytically-active noble metal (e.g., at least one of Pt, Rh, Pd, Ru, and Ir). The inner pump electrode 22 also contains a noble metal (e.g., Au) having a catalytic-activity inhibition ability for inhibiting the catalytic activity of the catalytically-active noble metal against the specific gas. Accordingly, the inner pump electrode 22 that comes into contact with the measurement-object gas is composed of a material with a weakened reduction ability against the specific gas (i.e., NOx) component of the measurement-object gas. The inner pump electrode 22 is preferably formed of a cermet containing a noble metal and an oxygen-ion-conductive oxide (i.e., $ZrO_2$). Moreover, the inner pump electrode 22 is preferably porous. In this embodiment, the inner pump electrode 22 is a porous cermet electrode composed of Pt and $ZrO_2$ and containing 1% Au.

Similar to the inner pump electrode 22, the outer pump electrode 23 contains a catalytically-active noble metal. Similar to the inner pump electrode 22, the outer pump electrode 23 may contain a noble metal having a catalytic-activity inhibition ability, and may be formed of a cermet. The outer pump electrode 23 is preferably porous. In this embodiment, the outer pump electrode 23 is a porous cermet electrode composed of Pt and $ZrO_2$.

In the main pump cell 21, the desired pump voltage Vp0 is applied between the inner pump electrode 22 and the outer pump electrode 23 so that a pump current Ip0 flows between the inner pump electrode 22 and the outer pump electrode 23 in either a positive or negative direction. Thus, oxygen can be pumped from the first internal cavity 20 to the external space or from the external space to the first internal cavity 20.

To detect the oxygen concentration (oxygen partial pressure) in the atmosphere in the first internal cavity 20, the inner pump electrode 22, the second solid electrolyte layer 6, the spacer layer 5, the first solid electrolyte layer 4, the third substrate layer 3, and the reference electrode 42 form an electrochemical sensor cell, namely, an oxygen-partial-pressure detection sensor cell 80 for main pump control.

The oxygen concentration (oxygen partial pressure) in the first internal cavity 20 can be determined by measuring an electromotive force (voltage V0) in the main-pump-control oxygen-partial-pressure detection sensor cell 80. Furthermore, feedback control is performed on the pump voltage Vp0 of a variable power source 24 such that the voltage V0 becomes a target value, whereby the pump current Ip0 is controlled. Accordingly, the oxygen concentration in the first internal cavity 20 can be maintained at a predetermined fixed value.

The third diffusion control section 30 creates a predetermined diffusion resistance to the measurement-object gas whose oxygen concentration (oxygen partial pressure) has been controlled in the first internal cavity 20 by the operation of the main pump cell 21 and guides the measurement-object gas into the second internal cavity 40.

The second internal cavity 40 is provided as a space for further adjusting, using an auxiliary pump cell 50, the oxygen concentration (oxygen partial pressure) of the measurement-object gas introduced through the third diffusion control section 30 after the oxygen partial pressure is adjusted in advance in the first internal cavity 20. Thus, the oxygen concentration in the second internal cavity 40 can be maintained at a constant value with high accuracy so that the gas sensor 100 can measure the NOx concentration with high accuracy.

The auxiliary pump cell 50 is an auxiliary electrochemical pump cell composed of an auxiliary pump electrode 51 having a ceiling electrode portion 51a disposed over substantially an entire portion of the lower surface of the second solid electrolyte layer 6 that faces the second internal cavity 40, the outer pump electrode 23 (the outer electrode is not limited to the outer pump electrode 23, but may be any suitable electrode outside the sensor element 101), and the second solid electrolyte layer 6.

The auxiliary pump electrode 51 is disposed within the second internal cavity 40 in a tunnel-like structure similar to the aforementioned inner pump electrode 22 provided in the first internal cavity 20. Specifically, the tunnel-like structure is formed such that the second solid electrolyte layer 6 that provides a ceiling surface for the second internal cavity 40 is provided with the ceiling electrode 51a, the first solid electrolyte layer 4 that provides a bottom surface for the second internal cavity 40 is provided with a bottom electrode 51b, and side electrodes (not shown) that connect the ceiling electrode 51a and the bottom electrode 51b are formed on opposite wall surfaces of the spacer layer 5 that provide sidewalls for the second internal cavity 40. The auxiliary pump electrode 51 is similar to the inner pump electrode 22 in being formed by using a material with a weakened reduction ability against the $NO_x$ component in the measurement-object gas.

In detail, the auxiliary pump electrode 51 contains a catalytically-active noble metal (e.g., at least one of Pt, Rh, Pd, Ru, and Ir). The auxiliary pump electrode 51 also contains a noble metal (e.g., Au) having the aforementioned catalytic-activity inhibition ability. The auxiliary pump electrode 51 is preferably formed of a cermet containing a noble metal and an oxygen-ion-conductive oxide (i.e., $ZrO_2$). Moreover, the auxiliary pump electrode 51 is preferably porous. In this embodiment, the auxiliary pump electrode 51 is a porous cermet electrode composed of Pt and $ZrO_2$ and containing 1% Au.

In the auxiliary pump cell 50, the desired voltage Vp1 is applied between the auxiliary pump electrode 51 and the outer pump electrode 23. Thus, oxygen can be pumped from the atmosphere in the second internal cavity 40 to the external space or from the external space to the second internal cavity 40.

To control the oxygen partial pressure in the atmosphere in the second internal cavity 40, the auxiliary pump electrode 51, the reference electrode 42, the second solid electrolyte layer 6, the spacer layer 5, the first solid electrolyte layer 4, and the third substrate layer 3 form an electrochemical sensor cell, namely, an oxygen-partial-pressure detection sensor cell 81 for auxiliary pump control.

The auxiliary pump cell 50 performs pumping in accordance with a variable power source 52 that is voltage-controlled based on an electromotive force (voltage V1) detected by the auxiliary-pump-control oxygen-partial-pressure detection sensor cell 81. Accordingly, the oxygen partial pressure in the atmosphere within the second internal cavity 40 is controlled to a low partial pressure that substantially has no effect on $NO_x$ measurement.

In addition, a pump current Ip1 is used for controlling the electromotive force of the main-pump-control oxygen-partial-pressure detection sensor cell 80. In detail, the pump current Ip1 is input as a control signal to the main-pump-control oxygen-partial-pressure detection sensor cell 80, and the voltage V0 thereof is controlled, whereby the gradient of the oxygen partial pressure in the measurement-object gas introduced to the second internal cavity 40 from the third diffusion control section 30 is controlled to be constantly fixed. In the case of application as a $NO_x$ sensor, the oxygen concentration within the second internal cavity 40 is maintained at a fixed value of about 0.001 ppm in accordance with the functions of the main pump cell 21 and the auxiliary pump cell 50.

The fourth diffusion control section 60 creates predetermined diffusion resistance to the measurement-object gas whose oxygen concentration (oxygen partial pressure) has been controlled in the second internal cavity 40 by the operation of the auxiliary pump cell 50 and guides the measurement-object gas into the third internal cavity 61. The fourth diffusion control section 60 functions to limit the amount of NOx flowing into the third internal cavity 61.

The third internal cavity 61 is provided as a space for processing associated with the measurement of the nitrogen oxide (NOx) concentration in the measurement-object gas introduced through the fourth diffusion control section 60 after the oxygen concentration (oxygen partial pressure) is adjusted in advance in the second internal cavity 40. NOx concentration measurement is mainly performed in the third internal cavity 61 by the operation of a measurement pump cell 41.

The measurement pump cell 41 measures the $NO_x$ concentration in the measurement-object gas within the third internal cavity 61. The measurement pump cell 41 is an electrochemical pump cell constituted of a measurement electrode 44 provided on the upper surface of the first solid electrolyte layer 4 facing the third internal cavity 61, the outer pump electrode 23, the second solid electrolyte layer 6, the spacer layer 5, and the first solid electrolyte layer 4. The measurement electrode 44 is a porous cermet electrode composed of a material with an enhanced reduction ability against the $NO_x$ component in the measurement-object gas than the inner pump electrode 22. The measurement electrode 44 also functions as a $NO_x$ reduction catalyst that reduces the $NO_x$ existing in the atmosphere within the third internal cavity 61.

In detail, the measurement electrode 44 contains a catalytically-active noble metal (e.g., at least one of Pt, Rh, Pd, Ru, and Ir). The content of a noble metal having the aforementioned catalytic-activity inhibition ability in the measurement electrode 44 is smaller than the content thereof in the main pump cell 21 and the auxiliary pump electrode 51. The measurement electrode 44 preferably does not contain a noble metal having the catalytic-activity inhibition ability. The measurement electrode 44 is preferably formed of a cermet containing a noble metal and an oxygen-ion-conductive oxide (i.e., $ZrO_2$). Moreover, the measurement electrode 44 is preferably porous. In this embodiment, the measurement electrode 44 is a porous cermet electrode composed of Pt, Rh, and $ZrO_2$.

The measurement pump cell 41 pumps out oxygen produced by the decomposition of nitrogen oxide in the atmosphere around the measurement electrode 44. The amount of oxygen produced can be detected as a pump current Ip2.

Furthermore, in order to detect the oxygen partial pressure around the measurement electrode 44, the first solid electrolyte layer 4, the third substrate layer 3, the measurement electrode 44, and the reference electrode 42 constitute an electrochemical sensor cell, that is, a measurement-pump-control oxygen-partial-pressure detection sensor cell 82. A pulse power source 46 is controlled based on an electromotive force (voltage V2) detected by the measurement-pump-control oxygen-partial-pressure detection sensor cell 82. The pulse power source 46 applies the pump current Ip2, which is repeatedly on-off controlled, between the measurement electrode 44 and the outer pump electrode 23. The pulse power source 46 serves as an electric current source. The measurement pump cell 41 operates in accordance with this pump current Ip2.

The measurement-object gas introduced to the second internal cavity 40 reaches the measurement electrode 44 in the third internal cavity 61 via the fourth diffusion control section 60 under a condition where the oxygen partial pressure is controlled. The nitrogen oxide in the measurement-object gas surrounding the measurement electrode 44 is reduced ($2NO \rightarrow N_2+O_2$), so that oxygen is produced. Then, the produced oxygen is to undergo pumping by the measurement pump cell 41. During the pumping of the oxygen, the pump current Ip2 applied by the pulse power source 46 is controlled such that the voltage V2 detected by the measurement-pump-control oxygen-partial-pressure detection sensor cell 82 reaches a target state. Because the amount of oxygen produced around the measurement electrode 44 is proportional to the concentration of the nitrogen oxide in the measurement-object gas, the nitrogen oxide concentration in the measurement-object gas is calculated by using the pump current Ip2 in the measurement pump cell 41.

An oxygen-partial-pressure detection device serving as an electrochemical sensor cell may be constituted by combining the measurement electrode 44, the first solid electrolyte layer 4, the third substrate layer 3, and the reference electrode 42. Thus, an electromotive force according to a difference between the amount of oxygen produced as a result of reduction of the NOx component in the atmosphere surrounding the measurement electrode 44 and the amount of oxygen contained in reference air can be detected, so that the concentration of the NOx component in the measurement-object gas can be determined accordingly.

Furthermore, the second solid electrolyte layer 6, the spacer layer 5, the first solid electrolyte layer 4, the third substrate layer 3, the outer pump electrode 23, and the reference electrode 42 constitute an electrochemical sensor cell 83. The oxygen partial pressure in the measurement-object gas outside the sensor can be detected in accordance with an electromotive force (voltage Vref) obtained by the sensor cell 83.

In the gas sensor 100 having the above configuration, the measurement pump cell 41 receives the measurement-object gas whose oxygen partial pressure is constantly maintained at a fixed low value (i.e., a value that substantially has no effect on $NO_x$ measurement) as a result of actuation of the main pump cell 21 and the auxiliary pump cell 50. Thus, the $NO_x$ concentration in the measurement-object gas can be ascertained based on the pump current Ip2, used by the measurement pump cell 41 for pumping out oxygen produced by $NO_x$ reduction, substantially in proportion to the $NO_x$ concentration in the measurement-object gas.

To increase the oxygen ion conductivity of the solid electrolyte, the sensor element 101 further includes a heater section 70 that functions as a temperature regulator to heat and maintain the temperature of the sensor element 101. The heater section 70 includes a heater connector electrode 71, a heater 72, a through-hole 73, a heater insulating layer 74, and a pressure relief vent 75.

The heater connector electrode 71 is formed in contact with the lower surface of the first substrate layer 1. The heater connector electrode 71 is connected to an external power supply so that the heater section 70 can be externally powered.

The heater 72 is an electrical resistor formed between the second substrate layer 2 and the third substrate layer 3. The heater 72 is connected to the heater connector electrode 71 through the through-hole 73. The heater 72 is externally powered through the heater connector electrode 71 to generate heat, thereby heating and maintaining the temperature of the solid electrolyte forming the sensor element 101.

The heater 72 is embedded over the entire region from the first internal cavity 20 to the third internal cavity 61 so that the temperature of the entire sensor element 101 can be adjusted to a temperature that activates the solid electrolyte.

The heater insulating layer 74 is an insulating layer covering the upper and lower surfaces of the heater 72 and formed of an insulator such as alumina. The heater insulating layer 74 is formed in order to ensure electrical insulation between the second substrate layer 2 and the heater 72 and electrical insulation between the third substrate layer 3 and the heater 72.

The pressure relief vent 75 extends through the third substrate layer 3 and the air introduction layer 48 so as to communicate with the reference gas introduction space 43. The pressure relief vent 75 is formed in order to mitigate an increase in internal pressure due to a temperature increase in the heater insulating layer 74.

The controller 90 is a microprocessor including, for example, a CPU 92 and a memory 94. The controller 90 receives the voltage V0 detected by the main-pump-control oxygen-partial-pressure detection sensor cell 80, the voltage V1 detected by the auxiliary-pump-control oxygen-partial-pressure detection sensor cell 81, the voltage V2 detected by the measurement-pump-control oxygen-partial-pressure detection sensor cell 82, the voltage Vref detected by the sensor cell 83, the pump current Ip0 detected by the main pump cell 21, and the pump current Ip1 detected by the auxiliary pump cell 50. Furthermore, the controller 90 outputs control signals to the variable power source 24 of the main pump cell 21, the variable power source 52 of the auxiliary pump cell 50, and the pulse power source 46 of the measurement pump cell 41, so as to control the cells 21, 50, and 41.

The controller 90 performs feedback control on the pump voltage Vp0 of the variable power source 24 based on the voltage V0 so as to set the voltage V0 to a target value (referred to as "target value V0*") (i.e., to set the oxygen concentration in the first internal cavity 20 to a target concentration). Thus, the pump current Ip0 varies depending on the concentration of oxygen contained in the measurement-object gas.

The controller 90 also performs feedback control on the voltage Vp1 of the variable power source 52 based on the voltage V1 so as to set the voltage V1 to a target value (referred to as "target value V1*") (i.e., to set the oxygen concentration in the second internal cavity 40 to a predetermined low oxygen concentration that substantially has no effect on $NO_x$ measurement). In addition, the controller 90 sets the target value V0* of the voltage V0 (i.e., performs feedback control) based on the pump current Ip1 so as to set the pump current Ip1 flowing in accordance with the voltage Vp1 to a target value (referred to as "target value Ip1*"). Accordingly, the gradient of the oxygen partial pressure in the measurement-object gas introduced to the second internal cavity 40 from the third diffusion control section 30 is controlled to be constantly fixed. Moreover, the oxygen partial pressure in the atmosphere within the second internal cavity 40 is controlled to a low partial pressure that substantially has no effect on $NO_x$ measurement.

Moreover, the controller 90 performs feedback control on the pump current Ip2 of the pulse power source 46 based on the voltage V2 so as to set the voltage V2 to a target value (referred to as "target value V2*") (i.e., to set the oxygen concentration in the third internal cavity 61 to a predetermined low concentration). Thus, oxygen produced as a result of reduction of the NOx in the measurement-object gas in the third internal cavity 61 is pumped out from the third internal cavity 61 such that the oxygen becomes substantially zero. Then, the controller 90 determines the $NO_x$ concentration in the measurement-object gas based on the pump current Ip2 serving as a value according to the oxygen produced in the third internal cavity 61 from the specific gas (i.e., NOx).

The memory 94 stores therein, for example, a relational expression (e.g., a linear function) or a map as a correspondence relationship between the pump current Ip2 and the $NO_x$ concentration. Such a relational expression or a map can be preliminarily obtained from tests.

An example of how the gas sensor 100 having the above-described configuration is used will be described below. It is assumed that the CPU 92 of the controller 90 is controlling the pump cells 21, 41, and 50 described above and is acquiring the voltages V0, V1, V2, and Vref from the sensor cells 80 to 83 described above. In this state, when the measurement-object gas is introduced through the gas inlet 10, the measurement-object gas first passes through the first diffusion control section 11, the buffer space 12, and the second diffusion control section 13 and reaches the first internal cavity 20. Then, the oxygen concentration in the measurement-object gas is adjusted by the main pump cell 21 and the auxiliary pump cell 50 in the first internal cavity 20 and the second internal cavity 40. After the adjustment, the measurement-object gas reaches the third internal cavity 61. The CPU 92 then detects the NOx concentration in the measurement-object gas based on the pump current Ip2 and the correspondence relationship stored in the memory 94.

Figure 3:
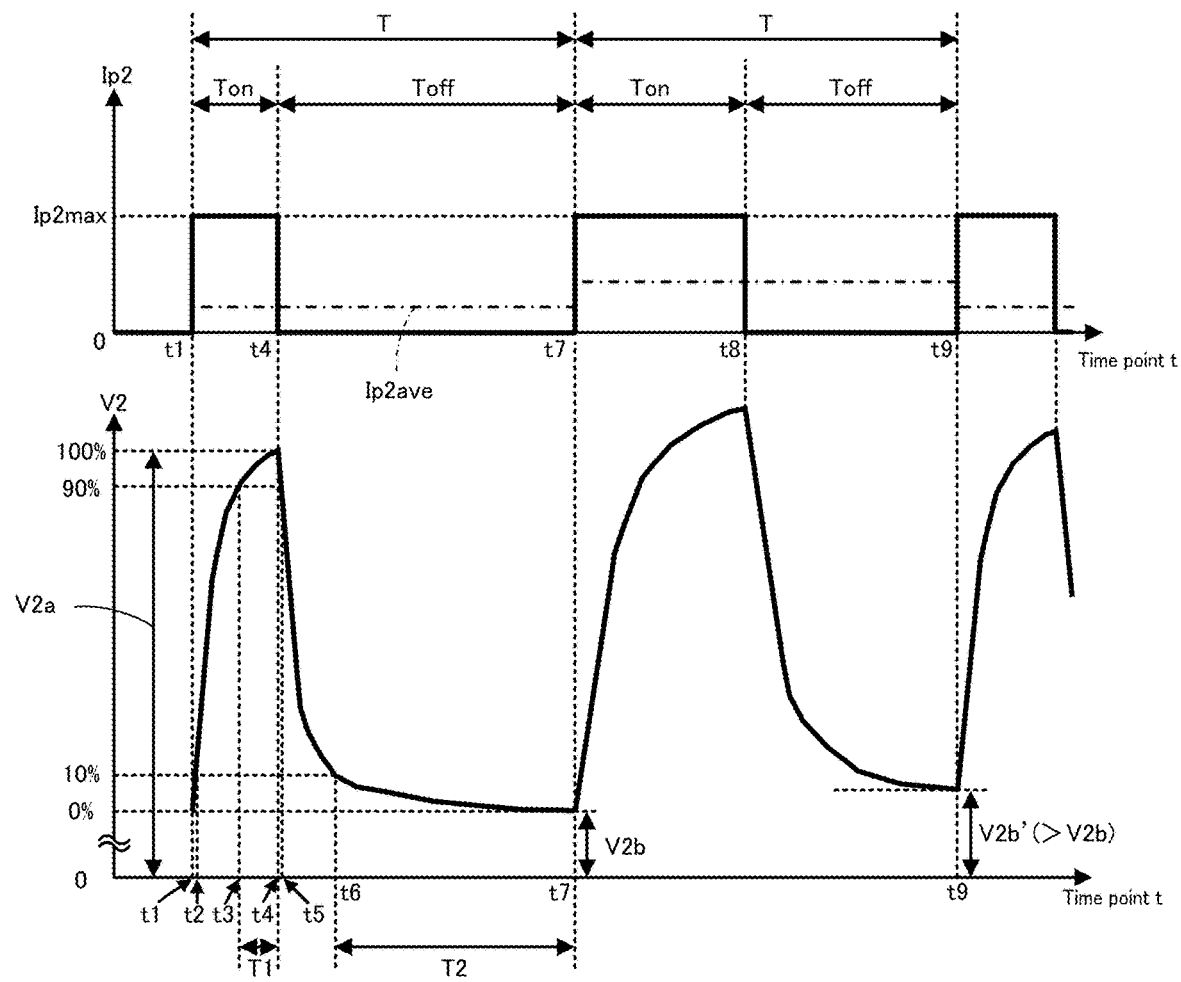
FIG. 3 illustrates temporal changes in a pump current Ip2 and a voltage V2.

The operation of the measurement pump cell 41 and the control of the measurement pump cell 41 by the controller 90 will be described here in detail. FIG. 3 illustrates temporal changes in the pump current Ip2 and the voltage V2. The upper section of FIG. 3 indicates the temporal change in the pump current Ip2, and the lower section indicates the temporal change in the voltage V2. With regard to the pump current Ip2, the direction in which oxygen can be pumped out from around the measurement electrode 44 to around the outer pump electrode 23 is defined as "positive". In FIG. 3, the upward direction of the ordinate axis is defined as "positive direction". The positive direction of the pump current Ip2 is the direction of an arrow of the pump current Ip2 in FIG. 1, and is the direction in which electric current flows from the measurement electrode 44 toward the outer pump electrode 23 at the outer side of the sensor element 101. With regard to the voltage V2, a state where the electric potential of the reference electrode 42 is higher than that of the measurement electrode 44 is defined as "positive". In FIG. 3, the upward direction of the ordinate axis is defined as "positive direction".

The pulse power source 46 of the measurement pump cell 41 applies the repeatedly on-off controlled pump current Ip2, that is, the intermittent pump current Ip2, between the measurement electrode 44 and the outer pump electrode 23, so that oxygen is pumped out from around the measurement electrode 44. In this embodiment, as shown in FIG. 3, the pump current Ip2 is a pulse-wave electric current that is repeatedly on-off controlled in cycles T. For example, when the pump current Ip2 rises from 0 A at a time point t1 and transitions to an on mode, the pump current Ip2 becomes a maximum current Ip2max and maintains this state until an ON time Ton elapses and a time point t4 is reached. When the pump current Ip2 falls at the time point t4 and transitions to an off mode, the pump current Ip2 becomes 0 A until an OFF time Toff elapses and a time point t7 is reached. Although the actual pump current Ip2 requires a short period of time for rising from the time point t1 and for falling from the time point t4, this is omitted in FIG. 3. Moreover, there may be a case where electric current slightly flows due to the effect of, for example, noise even while the pump current Ip2 output from the pulse power source 46 is in the off mode. However, such a case is omitted in FIG. 3.

As mentioned above, the CPU 92 of the controller 90 performs feedback control on the pump current Ip2 of the pulse power source 46 based on the voltage V2 so as to set the oxygen concentration in the third internal cavity 61 to the predetermined low concentration. An amount of oxygen that the measurement pump cell 41 pumps out from the third internal cavity 61 during one cycle (i.e., cycle T) in accordance with the pump current Ip2 is proportional to an average value Ip2ave (see a single-dot chain line in the upper section of FIG. 3) of the pump current Ip2 during one cycle. Therefore, for example, the CPU 92 varies the average value Ip2ave by outputting a control value to the pulse power source 46 to change at least one of parameters including the proportion (i.e., duty ratio) of the ON time Ton occupying the cycle T, the cycle T, and the maximum current Ip2max. Alternatively, the CPU 92 may output the average value Ip2ave as a control value to the pulse power source 46, and the pulse power source 46 may vary at least one of the aforementioned parameters based on the control value. In this embodiment, the CPU 92 outputs the duty ratio (or a variation of the duty ratio) as a control value to the pulse power source 46, and the pulse power source 46 varies the duty ratio of the pump current Ip2 based on the control value. For example, if the voltage V2 is smaller than the target value V2*, the CPU 92 controls the pulse power source 46 to increase the duty ratio of the pump current Ip2 (i.e., to extend the ON time Ton without changing the cycle T), thereby reducing the oxygen concentration in the third internal cavity 61. FIG. 3 shows an example where the second ON time Ton (between time points t7 and t8) is twice as long as the first ON time Ton (between the time points t1 and t4), such that the average value Ip2ave in the second cycle T is twice as large as that in the first cycle T. FIG. 3 also shows that, with the average value Ip2ave being doubled, the oxygen concentration in the third internal cavity 61 is reduced, such that the voltage V2 is higher with a value V2b' at a time point t9 than a value V2b at the time point t7.

The pump current Ip2 controlled by the CPU 92 in this manner ultimately becomes an electric current according to the oxygen produced in the third internal cavity 61 from the specific gas (i.e., NOx). Therefore, the CPU 92 can determine the NOx concentration in the measurement-object gas based on this pump current Ip2. For example, a value of a parameter (i.e., duty ratio) of the pump current Ip2 used as a control value by the CPU 92 is proportional to the NOx concentration in the measurement-object gas. Therefore, by storing the correspondence relationship between the two in the memory 94, the CPU 92 can determine the NOx concentration based on the control value output to the pulse power source 46 by the CPU 92 and the correspondence relationship stored in the memory 94. Likewise, the CPU 92 can also determine the NOx concentration by using a value (e.g., average value Ip2ave) determined based on the control value.

Figure 4:
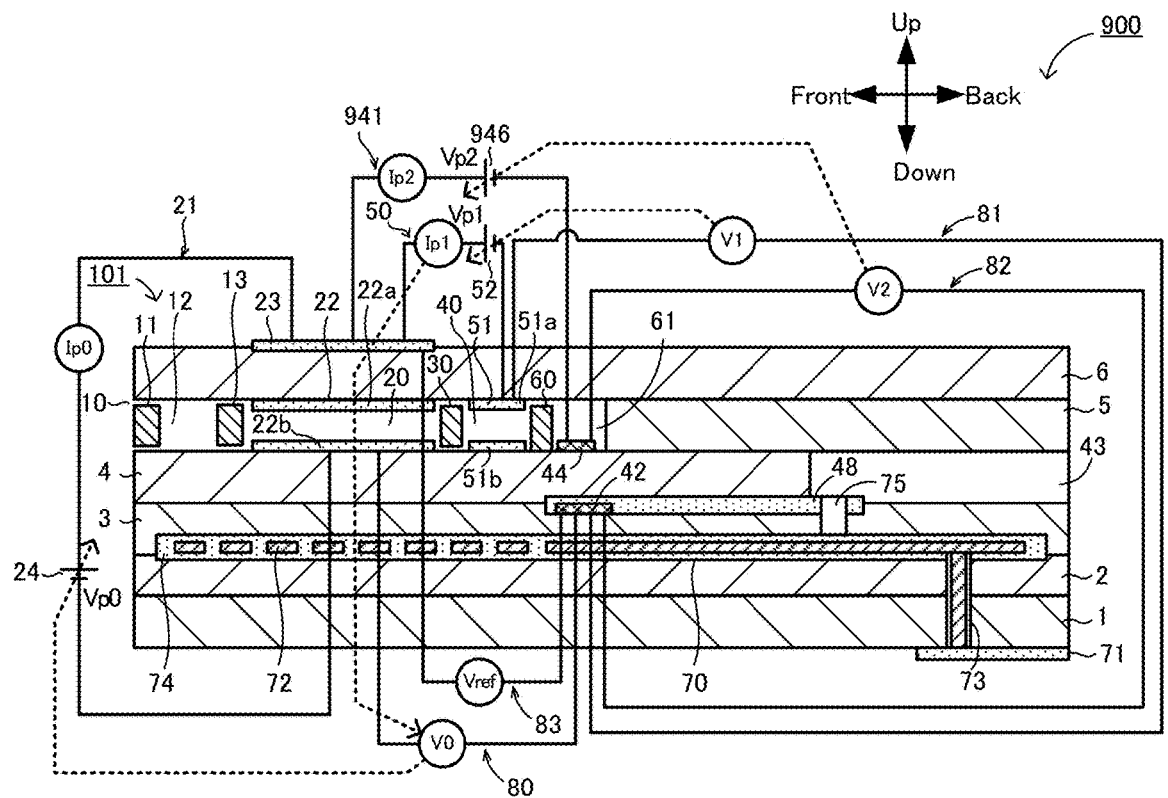
FIG. 4 is a schematic cross-sectional view of a gas sensor 900 according to a comparative example.
Figure 5:
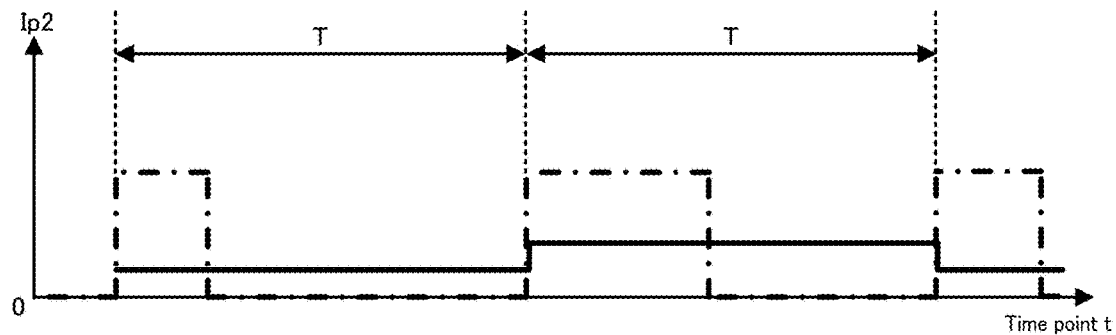
FIG. 5 illustrates a temporal change in the pump current Ip2 of the gas sensor 900.

The following description relates to a comparative example where the pump current Ip2 is a continuous electric current. FIG. 4 is a schematic cross-sectional view of a gas sensor 900 according to a comparative example. FIG. 5 illustrates a temporal change in the pump current Ip2 of the gas sensor 900. Components of the gas sensor 900 that are identical to those of the gas sensor 100 are given the same reference signs as those in FIG. 1, and detailed descriptions thereof will be omitted. The definition of the direction of the pump current Ip2 is the same as that of the gas sensor 100, and the upward direction of the ordinate axis in FIG. 5 is defined as "positive direction". Furthermore, in FIG. 5, the waveform of the pump current Ip2 shown in FIG. 3 is indicated by a single-dot chain line as a comparison. The gas sensor 900 includes a measurement pump cell 941 in place of the measurement pump cell 41. The measurement pump cell 941 is similar to the measurement pump cell 41 except that the measurement pump cell 941 includes a variable power source 946 in place of the pulse power source 46. The variable power source 946 applies a pump voltage Vp2 between the measurement electrode 44 and the outer pump electrode 23. Accordingly, the measurement pump cell 941 receives a continuous pump current Ip2, as shown in FIG. 5. A controller of the gas sensor 900 is not shown, but is similar to the controller 90 in that the controller receives the voltages V0, V1, V2, and Vref and the pump currents Ip0 and Ip1 and outputs control signals to the variable power sources 24 and 52. Furthermore, the controller of the gas sensor 900 performs feedback control on the pump voltage Vp2 of the variable power source 946 based on the input voltage V2 so as to set the voltage V2 to a target value. Thus, oxygen produced as a result of reduction of the NOx in the measurement-object gas in the third internal cavity 61 is pumped out from the third internal cavity 61 by the measurement pump cell 941 such that the oxygen becomes substantially zero. For example, when the controller is to perform feedback control on the pump voltage Vp2 at every cycle T identical to that in FIG. 3, the pump current Ip2 flowing to the measurement pump cell 941 changes at every cycle T, as shown in FIG. 5, while flowing continuously. Although the actual pump current Ip2 requires a short period of time to completely change at every cycle T, this is omitted in FIG. 5. The controller of the gas sensor 900 then acquires the pump current Ip2 from the measurement pump cell 941 and calculates the NOx concentration in the measurement-object gas based on this pump current Ip2.

If the average value Ip2ave in FIG. 3 and the pump current Ip2 indicated by a solid line in FIG. 5 are the same, the amount of oxygen pumped out from the third internal cavity 61 at every cycle T is the same. Therefore, even in a case where the pump current Ip2 is applied intermittently as in this embodiment instead of the pump current Ip2 being applied continuously as in the comparative example, the CPU 92 can still adjust the oxygen concentration in the third internal cavity 61 and measure the NOx concentration. Moreover, because the gas sensor 100 uses the pulse power source 46 serving as an electric current source, the control value output to the pulse power source 46 by the CPU 92 is a value according to the pump current Ip2. Therefore, without having to receive the pump current Ip2 from the measurement pump cell 41, the CPU 92 can ascertain the pump current Ip2 based on the control value set by the CPU 92 and determine the NOx concentration.

In the gas sensor 100, the pump current Ip2 is intermittently applied to the measurement pump cell 41 so that a change in the catalytic activity of the measurement electrode 44 due to use of the gas sensor 100 can be suppressed, as compared with a case where the pump current Ip2 is continuously applied to the measurement pump cell 941, as in the gas sensor 900. A conceivable reason for this will be described below.

When oxygen is to be pumped out from around the measurement electrode 44 by applying the pump current Ip2 between the measurement electrode 44 and the outer pump electrode 23, the surrounding oxygen (i.e., oxygen mainly produced as a result of NOx reduction) turns into oxygen ions ($O_2 + 4e^- \rightarrow 2O^{2-}$) inside the measurement electrode 44. The oxygen ions serve as electron carriers and travel through the solid electrolyte layers (i.e., the layers 4 to 6) toward the outer pump electrode 23. During this process, if the pump current Ip2 is a continuous electric current, a reaction where some noble metals (i.e., Pt and Rh) in the measurement electrode 44 oxidize and a reaction where oxygen ions are released as a result of reduction of the oxidized noble metals (i.e., $PtO$, $PtO_2$, and $Rh_2O_3$) both occur. When both reactions reach a state of equilibrium, some of the noble metals in the measurement electrode 44 are in a constantly oxidized state. Since oxidized noble metals tend to evaporate more easily than before they are oxidized, the noble metals in the measurement electrode 44 tend to decrease with use of the gas sensor 900, thus causing the catalytic activity of the measurement electrode 44 to decrease. Moreover, the oxidization of the noble metals in the measurement electrode 44 may conceivably cause the microstructure of the measurement electrode 44 to change. This may conceivably cause the three-phase interface among the measurement electrode 44, the pores in the measurement electrode 44, and the first solid electrolyte layer 4 or the two-phase interface between the measurement electrode 44 and the first solid electrolyte layer 4 to decrease in surface area, thus causing the catalytic activity of the measurement electrode 44 to decrease.

On the other hand, the following description relates to a case where an intermittent pump current Ip2 is used in the gas sensor 100 and is intermittently applied to the measurement pump cell 41 such that the intermittent pump current Ip2 becomes an average electric current (i.e., average value Ip2ave) equal to the continuous pump current Ip2 in the gas sensor 900. In this case, the pump current Ip2 (i.e., maximum current Ip2max) applied to the measurement electrode 44 during an on mode (e.g., between the time points t1 and t4 in FIG. 3) in the gas sensor 100 is a value larger than the continuous pump current Ip2 in the gas sensor 900 (see FIGS. 3 and 5). Accordingly, the oxygen inside the measurement electrode 44 turns into ions and travel toward the outer pump electrode 23 more during the on mode of the intermittent pump current Ip2 than when the pump current Ip2 is applied continuously, so that the oxygen concentration inside the measurement electrode 44 decreases. In such a state where the oxygen concentration inside the measurement electrode 44 is low, the aforementioned noble metals in the measurement electrode 44 are less likely to oxidize, and rather, reduction of oxidized noble metals may occur. Thus, in the gas sensor 100, a decrease in the aforementioned noble metals in the measurement electrode 44 with use thereof is suppressed, as compared with the gas sensor 900. Furthermore, in the gas sensor 100, electric current hardly flows to the measurement electrode 44 when the pump current Ip2 is in an off mode (e.g., between the time points t4 and t7 in FIG. 3), so that oxidization of the aforementioned noble metals in the measurement electrode 44 is less likely to occur. As a result, in the gas sensor 100, oxidization of the noble metals in the measurement electrode 44 is suppressed in both an on mode and an off mode of the pump current Ip2. It is thus conceivable that a decrease in the catalytic activity of the measurement electrode 44 due to use of the gas sensor 100 is suppressed therein, as compared with the gas sensor 900. Since a lower catalytic activity of the measurement electrode 44 leads to suppressed NOx reduction in the third internal cavity 61, the pump current Ip2 (more specifically, the average value Ip2ave) decreases, thus resulting deteriorated sensitivity for detecting the NOx concentration. In the gas sensor 100 according to this embodiment, such deteriorated sensitivity for detecting the NOx concentration with use thereof can be suppressed. Therefore, the gas sensor 100 according to this embodiment can maintain the measurement accuracy over a long period of use, and can thus extend the lifespan thereof.

The voltage V2 is a voltage between the measurement electrode 44 and the reference electrode 42 and is basically a value according to the oxygen concentration in the third internal cavity 61. However, because the electric potential of the measurement electrode 44 changes intermittently when the pulse power source 46 intermittently applies the pump current Ip2 thereto, the voltage V2 also varies periodically in a pulsating manner in response to this effect. In detail, the waveform of the voltage V2 has a first period in which a change is occurring as a result of the pump current Ip2 being controlled to an on mode, and a second period in which the change has receded as a result of the pump current Ip2 being controlled to an off mode. For example, in FIG. 3, with regard to the voltage V2, a change begins (i.e., the voltage V2 begins to rise) from the time point t1, a value V2a (i.e., maximum value) corresponding to a maximum change is reached at the time point t4, the change begins to recede (i.e., the voltage V2 begins to fall) from the time point t4, and a value V2b (i.e., minimum value) where the change has receded the most is reached at the time point t7. In this case, the range from the value V2b to the value V2a of the voltage V2 during the duration of a single cycle T of the pump current Ip2 is defined as 0% to 100%, and the first period and the second period of the voltage V2 are set using this range as a reference. In detail, a period in which the voltage V2 is 90% or higher (i.e. between the time points t3 and t5) is defined as the first period, and the length thereof is defined as a first duration T1. A period from when the pump current Ip2 is controlled to an off mode and the voltage V2 becomes 10% or lower to when the voltage V2 begins to rise as a result of the pump current Ip2 being controlled to an on mode in the subsequent cycle (i.e. between the time points t6 and t7) is defined as a second period, and the length thereof is defined as a second duration T2. In FIG. 3, the voltage V2 reaches the value V2a corresponding to the first maximum change at the time point t4 at which the pump current Ip2 is controlled to an off mode. However, if the ON time Ton is long, there may be a case where the voltage V2 may reach the value V2a prior to the time point t4 and remain in this state until the time point t4.

Accordingly, in this embodiment, the voltage V2 varies periodically in response to the effect of the pump current Ip2. During the second period, the effect that the pump current Ip2 has on the voltage V2 is smaller, as compared with the first period. Therefore, the voltage V2 during the second period is a value that indicates the oxygen concentration in the third internal cavity 61 more accurately than the voltage V2 during the first period. Accordingly, the CPU 92 preferably performs the above-described control of the pump current Ip2 based on the voltage V2 during the second period. Thus, the CPU 92 can accurately set the oxygen concentration in the third internal cavity 61 close to the predetermined low concentration, and can also accurately determine the NOx concentration in the measurement-object gas. In this embodiment, the CPU 92 acquires the voltage V2 during the second period, compares the acquired voltage V2 with the target value V2*, and sets the control value to be output to the pulse power source 46. Furthermore, as shown in FIG. 3, the voltage V2 during the second period also changes with time, and the effect of the pump current Ip2 tends to decrease toward the end of the second period (i.e., the time point t7 in FIG. 3). This is conceivably due to the effect of a capacity component in the measurement pump cell 41, such as a capacity component of the measurement electrode 44. Thus, the CPU 92 preferably controls the pump current Ip2 based on the voltage V2 at the latest possible timing in the second period. For example, the CPU 92 may control the pump current Ip2 based on the voltage V2 at any timing in the latter half of the second period.

The CPU 92 may control the pump current Ip2 based on the voltage V2 during the second period in each of a plurality of cycles T (e.g., based on an average value of a plurality of voltages V2 acquired in different cycles). For example, if the pump current Ip2 is controlled based only on the voltage V2 during the second period in one cycle, the control of the pump current Ip2 may sometimes become unstable due to, for example, a fluctuation or a deviation of the actual average value Ip2ave relative to the proper average value Ip2ave corresponding to the NOx concentration. In contrast, the CPU 92 controls the pump current Ip2 based on, for example, the average value of the voltages V2 during the second periods in the plurality of cycles T, so that the control is less likely to become unstable. In this embodiment, the CPU 92 stores the voltage V2 in the memory 94 at a predetermined timing during the second period for every cycle T, and controls the pump current Ip2 based on an average value of multiple times' (e.g., three times') worth of most-recently-stored voltages V2.

The CPU 92 may control the main pump cell 21 based on the voltage V0 during the second period of the voltage V2. Likewise, the CPU 92 may control the auxiliary pump cell 50 based on the voltage V1 during the second period of the voltage V2. The CPU 92 may set the target value V0* based on the pump current Ip1 during the second period of the voltage V2.

The correspondence relationship between the components in this embodiment and the components in the present invention will now be clarified. The first substrate layer 1, the second substrate layer 2, the third substrate layer 3, the first solid electrolyte layer 4, the spacer layer 5, and the second solid electrolyte layer 6 according to this embodiment correspond to an element body according to the present invention. The main pump cell 21, the auxiliary pump cell 50, and the measurement pump cell 41 each correspond to a pump cell. The inner pump electrode 22, the auxiliary pump electrode 51, and the measurement electrode 44 each correspond to an inner electrode. The outer pump electrode 23 corresponds to an outer electrode. Furthermore, the inner pump electrode 22 corresponds to an inner main pump electrode, the auxiliary pump electrode 51 corresponds to an inner auxiliary pump electrode, the measurement electrode 44 corresponds to an inner measurement electrode, the outer pump electrode 23 corresponds to an outer main pump electrode, an outer auxiliary pump electrode, and an outer measurement electrode, and the third internal cavity 61 corresponds to a measurement chamber. Moreover, the pump current Ip2 corresponds to a measurement pump current, the voltage V2 corresponds to a measurement voltage, the measurement-pump-control oxygen-partial-pressure detection sensor cell 82 corresponds to a measurement-voltage detection device, and the controller 90 corresponds to a measurement-pump-cell control device and a specific-gas-concentration detection device.

The gas sensor 100 according to this embodiment described in detail above includes the main pump cell 21, the auxiliary pump cell 50, and the measurement pump cell 41 as one or more pump cells. The main pump cell 21 has the inner pump electrode 22 disposed in the first internal cavity 20 and also has the outer pump electrode 23, and pumps out oxygen from the first internal cavity 20. The auxiliary pump cell 50 has the auxiliary pump electrode 51 disposed in the second internal cavity 40 at the downstream side of the first internal cavity 20 and also has the outer pump electrode 23, and pumps out oxygen from the second internal cavity 40. The measurement pump cell 41 has the measurement electrode 44 disposed in the third internal cavity 61 at the downstream side of the second internal cavity 40 and also has the outer pump electrode 23, and pumps out oxygen produced in the third internal cavity 61 from NOx in the measurement-object gas. Of these pump cells, the measurement pump cell 41 applies the repeatedly on-off controlled pump current Ip2 between the measurement electrode 44 and the outer pump electrode 23, so as to pump out oxygen surrounding the measurement electrode 44. Accordingly, the gas sensor 100 can suppress a change (i.e., decrease) in the catalytic activity of the measurement electrode 44 with use thereof, as compared with a case where the pump current Ip2 is continuously applied between the measurement electrode 44 and the outer pump electrode 23, as in the gas sensor 900. The repeatedly on-off controlled pump current Ip2 has a higher peak value (i.e., maximum current Ip2max) than the continuous pump current Ip2, and thus achieves a high signal-to-noise ratio (S/N ratio) and is resistant to noise.

Of the pump cells 21, 50, and 41, the measurement pump cell 41 operates by using an intermittent pump current (i.e., pump current Ip2). A change in the catalytic activity of the measurement electrode 44 has a larger effect on the sensitivity for detecting the NOx concentration of the gas sensor 100 than a change in the catalytic activity of the inner pump electrode 22 and the auxiliary pump electrode 51. Therefore, deterioration in the detection sensitivity may be readily minimized by suppressing a change in the catalytic activity of the measurement electrode 44.

Furthermore, the CPU 92 controls the pump current Ip2 based on the voltage V2 during the second period so as to set the oxygen concentration in the third internal cavity 61 to the predetermined low concentration. Then, the CPU 92 detects the NOx concentration in the measurement-object gas based on the pump current Ip2. Accordingly, the CPU 92 can accurately detect the NOx concentration.

The present invention is not limited whatsoever to the above embodiment, and various embodiments are possible so long as they belong within the technical scope of the present invention.

Figure 6:
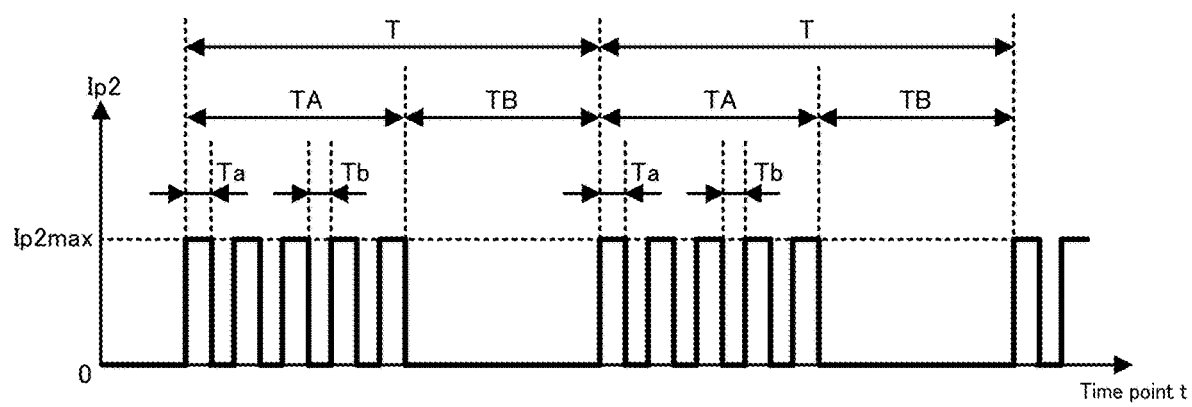
FIG. 6 illustrates an example where the pump current Ip2 is a burst pulse.

For example, although the intermittent pump current Ip2 is an electric current having one rectangular wave per cycle (i.e., a rectangular single pulse current) in the above-described embodiment, as shown in FIG. 3, the present invention is not limited thereto. For example, the pulse power source 46 may use a burst pulse current, as shown in FIG. 6, as the intermittent pump current Ip2. In this case, the CPU 92 may vary the average value Ip2ave of the pump current Ip2 during one cycle by outputting a control value to the pulse power source 46 to change at least one of parameters including the proportion (i.e., duty ratio) of an oscillation period TA occupying a cycle T (i.e., burst cycle), the cycle T, the number of pulses during one cycle (i.e., five pulses in FIG. 6), a time Ta of a single oscillation (i.e., pulse), a pulse cycle (Ta+Tb), and the maximum current Ip2max.

In the case where the pump current Ip2 is a burst pulse current, as in FIG. 6, the first period of the voltage V2 is included in the oscillation period TA, and the second period is included in a non-oscillation period TB. More specifically, in the case where the pump current Ip2 is a burst pulse current, the oscillation period TA is regarded as an on period (i.e., between the time points t1 and t4 in FIG. 3) of the pump current Ip2, the non-oscillation period TB is regarded as an off period (i.e., between the time points t4 and t7 in FIG. 3) of the pump current Ip2, and the second period is defined based on a method similar to that in the above-described embodiment.

Although the pulse power source 46 applies a rectangular-wave pulse current as the pump current Ip2 in the above-described embodiment, as shown in FIG. 3, the pulse current to be applied is not limited to a rectangular-wave (square-wave) pulse current and may have a sinusoidal half waveform, a triangular waveform, a saw-tooth waveform, or a waveform at the time of discharge, or may have a waveform obtained by combining one or more of these waveforms.

Although not specifically described in the above-described embodiment, each cycle T of the intermittent pump current Ip2 in FIGS. 3 and 6 may be, for example, 0.1 s or shorter (i.e., a frequency of 10 Hz or higher), 0.02 s or shorter (i.e., a frequency of 50 Hz or higher), or 0.001 s or shorter (i.e., a frequency of 100 Hz or higher). For example, in a case where the controller 90 outputs the determined NOx concentration to another device, such as an engine ECU of a vehicle, at every predetermined cycle Tout, the cycle T is preferably shorter than or equal to 1/10 of the cycle Tout.

Figure 7:
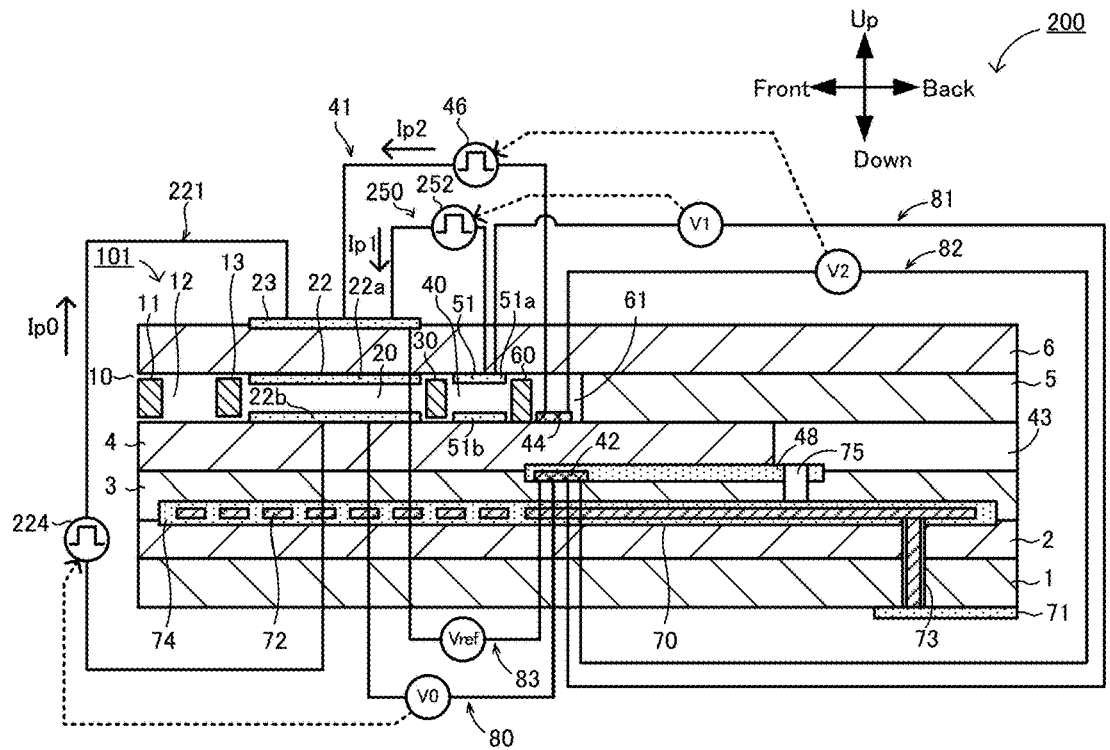
FIG. 7 is a schematic cross-sectional view of a gas sensor 200 according to a modification.

Although the measurement pump cell 41 among the pump cells 21, 50, and 41 included in the gas sensor 100 operates by using an intermittent pump current (i.e., pump current Ip2) in the above-described embodiment, the present invention is not limited thereto. At least one of the pump cells included in the gas sensor 100 may simply operate by using an intermittent pump current. For example, the main pump cell 21 and the measurement pump cell 41 may operate by using an intermittent pump current. FIG. 7 is a schematic cross-sectional view of a gas sensor 200 according to a modification. Components of the gas sensor 200 that are identical to those of the gas sensor 100 are given the same reference signs as those in FIG. 1, and detailed descriptions thereof will be omitted. The gas sensor 200 includes a main pump cell 221 in place of the main pump cell 21, and includes an auxiliary pump cell 250 in place of the auxiliary pump cell 50. The main pump cell 221 is similar to the main pump cell 21 except that the main pump cell 221 includes a pulse power source 224, serving as an electric current source similar to the pulse power source 46, in place of the variable power source 24. The auxiliary pump cell 250 is similar to the auxiliary pump cell 50 except that the auxiliary pump cell 250 includes a pulse power source 252, serving as an electric current source similar to the pulse power source 46, in place of the variable power source 52. In the gas sensor 200 according to this modification, the main pump cell 221 applies an intermittent pulse current so that a change in the catalytic activity of the inner pump electrode 22 due to use of the gas sensor 200 can be suppressed. Moreover, the pulse power source 252 applies an intermittent pulse current so that a change in the catalytic activity of the auxiliary pump electrode 51 due to use of the gas sensor 200 can be suppressed. As mentioned above, the inner pump electrode 22 contains a catalytically-active noble metal and a noble metal having the catalytic-activity inhibition ability. Therefore, when a noble metal in the inner pump electrode 22 oxidizes and evaporates, it is conceivable that the oxygen pumping performance of the main pump cell 21 may deteriorate due to a decrease in the catalytic activity of the inner pump electrode 22, or the inner pump electrode 22 may decompose the NOx in the first internal cavity 20 due to an increase in the catalytic activity. Since either case is not preferable for the gas sensor 200, it is significant to suppress such a change (i.e., an increase or decrease) in the catalytic activity of the inner pump electrode 22. The same applies to the auxiliary pump electrode 51. In a case where the main pump cell 221 is to pump oxygen into the first internal cavity 20 from around the outer pump electrode 23 by using an intermittent pulse current, it is conceivable that a change in the catalytic activity of the outer pump electrode 23 can be suppressed. For example, in a case where the oxygen concentration in the measurement-object gas is lower than the aforementioned target oxygen concentration in the first internal cavity 20 (including a case of a rich atmosphere), the controller 90 controls the pulse power source 224 such that the main pump cell 221 pumps oxygen into the first internal cavity 20 from around the outer pump electrode 23. In this case, the controller 90 may invert the positive and negative signs of pulses of the pulse power source 224, so as to switch between a mode where the main pump cell 221 pumps oxygen out from the first internal cavity 20 and a mode where the main pump cell 221 pumps oxygen into the first internal cavity 20. Accordingly, a negative pulse current (i.e., a pulse whose electric current value falls from zero to a negative value) may be applied, instead of a positive pulse current as in FIGS. 3 and 6.

Even in a case where a continuous pump current Ip0 is applied to the main pump cell 21 as in the above-described embodiment, an electric current source may be used in place of the variable power source 24, and the pump current Ip0 may be varied directly by the electric current source. Likewise, even in a case where a continuous pump current Ip1 is applied to the auxiliary pump cell 50 as in the above-described embodiment, an electric current source may be used in place of the variable power source 52, and the pump current Ip1 may be varied directly by the electric current source.

Figure 8:
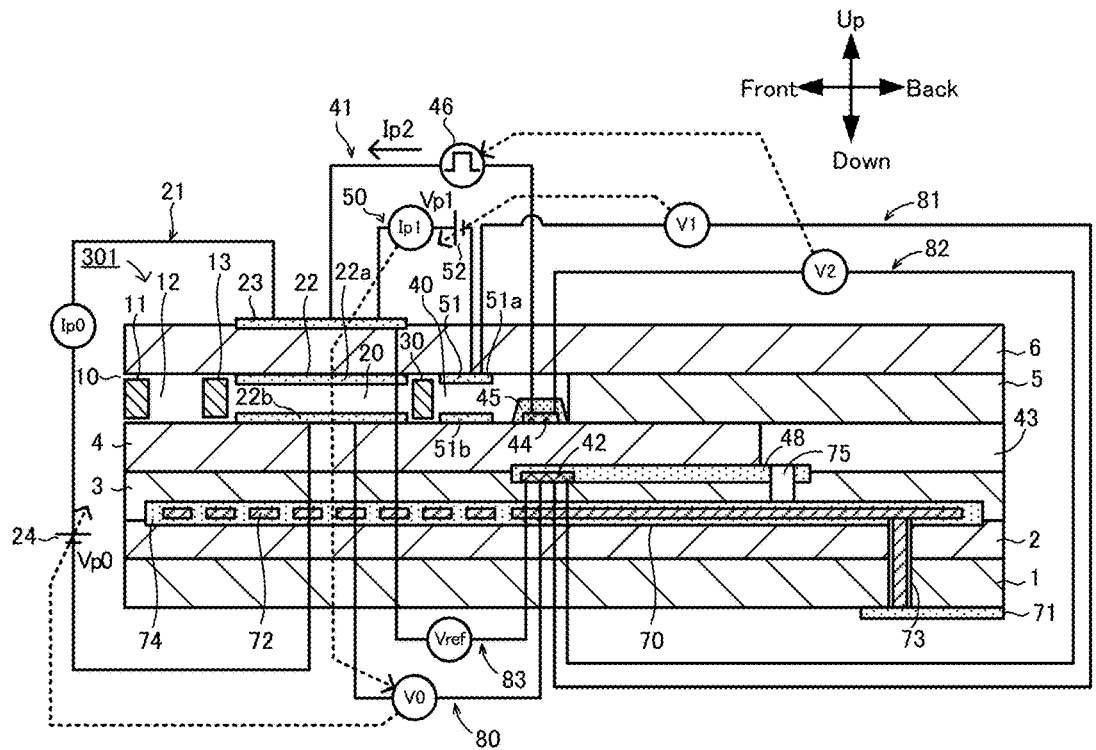
FIG. 8 is a schematic cross-sectional view of a sensor element 301 according to a modification.

Although the sensor element 101 of the gas sensor 100 includes the first internal cavity 20, the second internal cavity 40, and the third internal cavity 61 in the above-described embodiment, the present invention is not limited thereto. For example, the third internal cavity 61 may be omitted, as in a sensor element 301 in FIG. 8. In the sensor element 301 according to a modification shown in FIG. 8, the gas inlet 10, the first diffusion control section 11, the buffer space 12, the second diffusion control section 13, the first internal cavity 20, the third diffusion control section 30, and the second internal cavity 40 are provided next to each other in a communicating manner in that order between the lower surface of the second solid electrolyte layer 6 and the upper surface of the first solid electrolyte layer 4. The measurement electrode 44 is disposed on the upper surface of the first solid electrolyte layer 4 within the second internal cavity 40. The measurement electrode 44 is covered by a fourth diffusion control section 45. The fourth diffusion control section 45 is a film formed of a ceramic porous body composed of, for example, alumina ($Al_2O_3$). Similar to the fourth diffusion control section 60 according to the above-described embodiment, the fourth diffusion control section 45 has a function of limiting the amount of $NO_x$ flowing to the measurement electrode 44. Moreover, the fourth diffusion control section 45 also functions as a protective film for the measurement electrode 44. The ceiling electrode 51a of the auxiliary pump electrode 51 is provided to extend to a position directly above the measurement electrode 44. The sensor element 301 having such a configuration is similar to that in the above-described embodiment in being able to detect the NOx concentration based on the pump current Ip2. In this case, the space surrounding the measurement electrode 44 (i.e., the interior of the fourth diffusion control section 45) functions as a measurement chamber.

Although the outer pump electrode 23 serves as an outer main pump electrode of the main pump cell 21, an outer auxiliary pump electrode of the auxiliary pump cell 50, and an outer measurement electrode of the measurement pump cell 41 in the above-described embodiment, the present invention is not limited thereto. Any one or two of the outer main pump electrode, the outer auxiliary pump electrode, and the outer measurement electrode may be provided at the outer side of the sensor element 101 independently of the outer pump electrode 23.

Although the element body of the sensor element 101 according to the embodiment described above is a stack including a plurality of solid electrolyte layers (the layers 1 to 6), the present invention is not limited thereto. The element body of the sensor element 101 may include at least one oxygen-ion-conductive solid electrolyte layer and have a measurement-object gas flow section inside the element body. For example, the layers 1 to 5 other than the second solid electrolyte layer 6 in FIG. 1 may be layers formed of materials other than solid electrolytes (e.g., alumina layers). In this case, the electrodes of the sensor element 101 may be disposed on the second solid electrolyte layer 6. For example, the measurement electrode 44 in FIG. 1 may be disposed on the lower surface of the second solid electrolyte layer 6. In addition, the reference gas introduction space 43 may be disposed in the spacer layer 5 rather than in the first solid electrolyte layer 4. The air introduction layer 48 may be disposed between the second solid electrolyte layer 6 and the spacer layer 5 rather than between the first solid electrolyte layer 4 and the third substrate layer 3. The reference electrode 42 may be disposed on the lower surface of the second solid electrolyte layer 6 on the rear side of the third internal cavity 61.

Although the gas sensor 100 detects the NOx concentration as a specific gas concentration in the above-described embodiment, the specific gas concentration may alternatively be the concentration of another oxide. In a case where the specific gas is an oxide, oxygen is produced as a result of reduction of the specific gas itself in the third internal cavity 61, similarly to the above-described embodiment. Thus, the CPU 92 can detect the specific gas concentration based on a detection value (e.g., average value Ip2ave) according to this oxygen. Alternatively, the specific gas may be a non-oxide, such as ammonia. In a case where the specific gas is a non-oxide, the specific gas is converted into an oxide in, for example, the first internal cavity 20 (i.e., is converted into NO by being oxidized in the case of ammonia), so that oxygen is produced as a result of reduction of the oxide in the third internal cavity 61 after the conversion. Thus, the CPU 92 can acquire a detection value according to this oxygen and detect the specific gas concentration. Accordingly, whether the specific gas is an oxide or a non-oxide, the gas sensor 100 can detect the specific gas concentration based on oxygen produced in the third internal cavity 61 from the specific gas.

As an alternative to the above-described embodiment in which the controller 90 sets the target value V0* of the voltage V0 (i.e., performs feedback control) based on the pump current Ip1 so as to set the pump current Ip1 to the target value Ip1*, and performs feedback control on the pump voltage Vp0 so as to set the voltage V0 to the target value V0*, the controller 90 may perform another control. For example, the controller 90 may perform feedback control on the pump voltage Vp0 based on the pump current Ip1 so as to set the pump current Ip1 to the target value Ip1*.

Specifically, the controller 90 may omit the acquisition of the voltage V0 from the main-pump-control oxygen-partial-pressure detection sensor cell 80 and the setting of the target value V0* and may directly control the pump voltage Vp0 (and, by extension, the pump current Ip0) based on the pump current Ip1.

Although the pump voltage Vp2 of the pulse power source 46 is controlled such that the voltage V2 detected by the measurement-pump-control oxygen-partial-pressure detection sensor cell 82 becomes the target value V2*, and the NOx concentration in the measurement-object gas is calculated by using the pump current Ip2 at that time in the above-described embodiment, the present invention is not limited thereto. For example, the CPU 92 may perform feedback control on the measurement pump cell 41 (e.g., control the pump voltage Vp2) so as to set the average value Ip2ave shown in FIG. 3 to a predetermined target value Ip2*, and may calculate the NOx concentration by using the voltage V2 at that time. With the measurement pump cell 41 being controlled such that the average value Ip2ave becomes the target value Ip2*, oxygen is pumped out from the third internal cavity 61 at a substantially fixed flow rate on average, or in other words, in terms of a longer time period than the cycle T. Therefore, the oxygen concentration in the third internal cavity 61 changes in accordance with the amount of oxygen produced as a result of reduction of the NOx in the measurement-object gas in the third internal cavity 61, thus causing the voltage V2 to change accordingly. Accordingly, the voltage V2 becomes a value according to the NOx concentration in the measurement-object gas. Thus, the NOx concentration can be calculated based on this voltage V2. For example, the correspondence relationship between the voltage V2 and the NOx concentration may be preliminarily stored in the memory 94. Moreover, the CPU 92 uses the value of the voltage V2 during the second period as a value of the voltage V2 for calculating the NOx concentration. As mentioned above, the effect that the pump current Ip2 has on the voltage V2 is small during the second period. Therefore, the specific gas concentration in the measurement-object gas can be accurately detected by using the voltage V2 during the second period.

Figure 9:
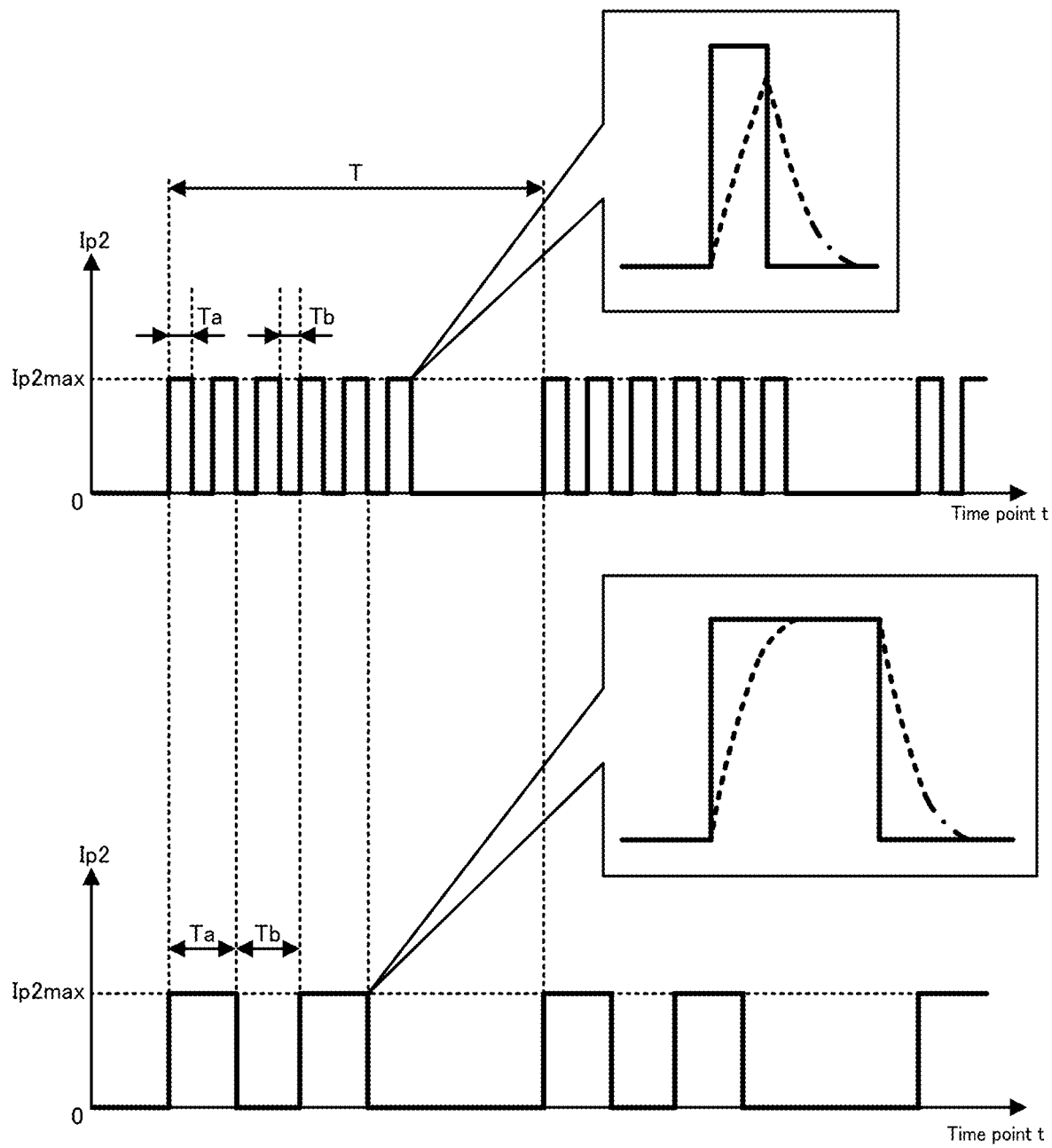
FIG. 9 illustrates a comparison between pulse currents having different pulse widths.
Figure 10:
FIG. 10 illustrates an example of comparison results between a case where control for reducing the number of pulses is not performed and a case where such control is performed.

In FIGS. 3 and 6 in the above-described embodiment, the electric current waveform is rectangular in a case where the pump current Ip1 is a pulse current. However, as mentioned above, a pulse current requires a short period of time for rising and falling. Specifically, a pulse current actually has a rise time and a fall time, and the waveform of a pulse current is not a perfect rectangle. Therefore, for example, as shown in an enlarged view of a pulse current in the upper section of FIG. 9, if the pulse width of the pulse current is too small, the actual peak value of the pulse current (i.e., the peak value of the waveform indicated by a dashed line) may sometimes not reach the peak value of an ideal rectangular waveform (i.e., the peak value of the waveform indicated by a solid line) due to the effect of the rise time. In this case, for example, even if the CPU 92 performs the aforementioned feedback control based on the voltage V2 and the target value V2* and outputs a control value to the pulse power source 46 so as to set the average value Ip2ave to a certain target value (referred to as "target average current Ip2ave*"), the actual average value Ip2ave becomes smaller than the theoretical average value Ip2ave, thus causing the actual average value Ip2ave to deviate from the target average current Ip2ave*. Thus, the controller 90 may sometimes be not able to properly control the measurement pump cell 41, or the S/N ratio of the pump current Ip2 may sometimes decrease. In contrast, for example, as shown in an enlarged view of a pulse current in the lower section of FIG. 9, if the pulse width of the pulse current is large, the actual peak value of the pulse current (i.e., the peak value of the waveform indicated by a dashed line) reaches the peak value of an ideal rectangular waveform (i.e., the peak value of the waveform indicated by a solid line) even with the existence of the rise time. Therefore, if the pulse width is large, the actual average value Ip2ave is less likely to deviate from the theoretical average value Ip2ave and the target average current Ip2ave*. Thus, the controller 90 preferably controls the measurement pump cell 41 such that the pulse width of the pump current Ip2 does not become too small to an extent that the actual peak value does not reach the peak value of the ideal rectangular waveform. In other words, the controller 90 preferably controls the pump current Ip2 in a range where the pulse width of the pump current Ip2 does not fall below a predetermined lower limit value. For example, if the target average current Ip2ave* is small, the controller 90 preferably reduces the number of pulses. By reducing the number of pulses, the pulse width is increased accordingly for applying the pump current Ip2 according to the target average current Ip2ave*, so that the pulse width can be prevented from decreasing. In the example in FIG. 9, the pulse width of the waveform in the upper section is small such that the average value Ip2ave and the target average current Ip2ave* deviate from each other. However, by using the waveform in the lower section as an alternative, the average value Ip2ave and the target average current Ip2ave* are less likely to deviate from each other. FIG. 9 illustrates a case where the pump current Ip2 is a burst pulse current, similar to FIG. 6, and the waveform in the upper section has six pulses per cycle, whereas the number of pulses in the waveform in the lower section is reduced to two. Instead, the pulse width (i.e., the time Ta per pulse) of the waveform in the lower section of FIG. 9 is three times that of the waveform in the upper section, so that the ideal average value Ip2ave is not varied between the waveform in the upper section and the waveform in the lower section. In the waveform in the lower section of FIG. 9, the burst-pulse interval (Tb in FIG. 9) is increased (specifically by a factor of 3). The following description relates to an example of a process performed by the controller 90 in a case where the number of pulses of the pump current Ip2 is reduced when the target average current Ip2ave* is small. For example, the controller 90 repeatedly executes a process involving setting the target average current Ip2ave* by performing feedback control based on the voltage V2 and the target value V2*, and controlling the measurement pump cell 41 so as to set the average value Ip2ave to the set target average current Ip2ave*. In this case, if the value of the set target average current Ip2ave* is a value included in a predetermined low current range (e.g., a value smaller than a predetermined threshold value), the measurement pump cell 41 is controlled such that a pump current Ip2 with a reduced number of pulses is applied, as compared with a case where the value of the set target average current Ip2ave* is a value not included in the predetermined low current range (e.g., a value larger than or equal to the predetermined threshold value). FIG. 10 illustrates an example of comparison results between a case where control for reducing the number of pulses is not performed (i.e., the table at the left side) and a case where such control is performed (i.e., the table at the right side). FIG. 10 shows the height, width, and number of pulses of the pump current Ip2 set by the controller 90 such that the average value Ip2ave becomes the target average current Ip2ave* in a case where the target average current Ip2ave* is varied between 0.06 µA and 6 µA. The pump current Ip2 is a burst pulse current, similar to FIGS. 6 and 9, the pulse height corresponds to Ip2max in FIGS. 6 and 9, the width corresponds to Ta in FIGS. 6 and 9, and the number of pulses corresponds to the number of pulses per cycle. Moreover, the presence and absence of a deviation between the actual average value Ip2ave and the target average current Ip2ave* in a case where the pump current Ip2 with the set pulse height, width, and number is applied is also shown. As shown at the left side of FIG. 10, in a case where the control for reducing the number of pulses is not performed and the number of pulses is fixed at 3, the set pulse width is a small value below 10 µs when the target average current Ip2ave* is lower than 0.15 µA. The actual average value Ip2ave in this case is smaller than the ideal average value Ip2ave and deviates from the target average current Ip2ave*. In contrast, in the example at the right side of FIG. 10, the controller 90 has performed the control for reducing the number of pulses to 1 when the target average current Ip2ave* is lower than 0.15 µA. As a result, when the target average current Ip2ave* is lower than 0.15 µA, the set number of pulses is reduced to 1, so that the pulse width is set to a value larger than or equal to 10 µs as a value required for achieving the target average current Ip2ave*. Specifically, the pulse width is set to a larger value than that in the table at the left side of FIG. 10, and the pulse width does not fall below 10 µs. As a result, even when the target average current Ip2ave* is lower than 0.15 µA, a deviation has not occurred between the actual average value Ip2ave and the target average current Ip2ave*. In FIG. 10, the NO concentration corresponding to the target average current Ip2ave* is also shown. In the example at the left side of FIG. 10, the actual average value Ip2ave deviates from the target average current Ip2ave* when the target average current Ip2ave* is lower than 0.15 µA, that is, when the NO concentration is a low concentration below 50 ppm, thus making it difficult to properly control the measurement pump cell 41, as mentioned above, or causing the S/N ratio of the pump current Ip2 to decrease. In contrast, in the example at the right side of FIG. 10, such a problem is less likely to occur even when the NO concentration is a low concentration below 50 ppm.

As mentioned above, the controller 90 preferably controls the pump current Ip2 in a range where the pulse width of the pump current Ip2 does not fall below the predetermined lower limit value. Likewise, the controller 90 preferably controls the pump current Ip2 in a range where the pulse interval (Tb in FIG. 9) of the pump current Ip2 does not fall below a predetermined lower limit value. This is because, in a case where the pulse interval is too small, a subsequent pulse may rise before the pulse current completely falls, thus causing a problem similar to the case where the pulse width is too small. In the examples in FIGS. 9 and 10, the pump current Ip2 is described as being a burst pulse current. Even in a case where the pump current Ip2 is not a burst pulse current, as in FIG. 3, it is preferable that the pump current Ip2 be controlled in a range where the pulse width (Ton in FIG. 3) and the pulse interval (Toff in FIG. 3) do not fall below the predetermined lower limit values.

Although the controller 90 and the power sources 24, 46, and 52 are illustrated separately from each other in FIG. 2 in the above-described embodiment, the power sources 24, 46, and 52 may be regarded as being a part of the controller 90.

EXAMPLES

Specific fabrication examples of gas sensors will be described below as practical examples. The present invention is not to be limited to the following practical examples.

Practical Example 1

Practical Example 1 is achieved by fabricating the gas sensor 100 shown in FIGS. 1 and 2. The sensor element 101 is fabricated as follows. First, ceramic green sheets corresponding to the individual layers 1 to 6 are each formed by mixing zirconia particles having 4 mol % of yttria added thereto as a stabilizer with an organic binder, a dispersant, a plasticizer, and an organic solvent, and then molding the mixture by tape molding. Then, the ceramic green sheets corresponding to the individual layers undergo hole-drilling, where appropriate, and screen-printing of a pattern of a conductive paste for forming electrodes and a circuit, and are subsequently stacked and pressure-bonded, so that a pressure-bonded body is obtained. A pattern for the measurement electrode 44 is formed by screen-printing a conductive paste having a mixture of zirconia particles and an organic binder onto Pt and Rh serving as noble metals. Then, an unbaked layered body having the size of the sensor element 101 is cut out from the pressure-bonded body and is baked, whereby the sensor element 101 is obtained. The fabricated sensor element 101 is electrically connected with the power sources and the controller 90, whereby the gas sensor 100 according to Practical Example 1 is fabricated. The pump current Ip2 to be applied by the pulse power source 46 is a rectangular single pulse current shown in FIG. 3, has a frequency of 100 Hz (i.e. a cycle T of 0.1 s), and a maximum current Ip2max of 50 µA.

Practical Example 2

In Practical Example 2, a gas sensor 100 similar to that in Practical Example 1 is fabricated except that the pump current Ip2 to be applied by the pulse power source 46 is changed. The pump current Ip2 to be applied by the pulse power source 46 is a burst pulse current shown in FIG. 6, has a frequency of 100 Hz (i.e. a cycle T of 0.1 s), has five pulses per cycle, and has 50% as the proportion (i.e., duty ratio) of the oscillation period TA occupying the cycle T (burst cycle).

Practical Example 3

In Practical Example 3, a gas sensor 100 similar to that in Practical Example 1 is fabricated except that the frequency is set to 200 Hz (i.e., the cycle T is set to 0.05 s).

Practical Example 4

In Practical Example 4, a gas sensor 100 similar to that in Practical Example 2 is fabricated except that the frequency is set to 200 Hz (i.e., the cycle T is set to 0.05 s).

Comparative Example 1

In Comparative Example 1, the gas sensor 900 according to the comparative example shown in FIG. 4 is fabricated. Specifically, in Comparative Example 1, the pump current Ip2 to be applied is a continuous electric current. The gas sensor 900 according to Comparative Example 1 is similar to that in Practical Example 1 except that the gas sensor 900 includes the measurement pump cell 941 shown in FIG. 4 in place of the measurement pump cell 41.

[Durability Test]

A durability test using a diesel engine is performed with respect to each of Practical Examples 1 to 4 and Comparative Example 1, and the degree of degradation in the measurement electrode 44 is evaluated. As indicators for evaluating the degree of degradation, the NO-sensitivity change rate before and after the durability test and the NO-sensitivity linear change rate before and after the durability test are measured. In detail, the test is performed as follows. The gas sensor according to Practical Example 1 is attached to an exhaust gas pipe of an automobile. Then, the temperature is set to 800° C. by applying electricity to the heater 72, thereby heating the sensor element 101. The controller 90 controls the aforementioned pump cells 21, 41, and 50 and acquires the voltages V0, V1, V2, and Vref from the aforementioned sensor cells 80 to 83. In this state, a first model gas having nitrogen as its base gas and having a NO concentration of 500 ppm is made to flow through the pipe. After waiting for a control value from the controller 90 to the pulse power source 46 to become stable, the average value Ip2ave is measured as an initial value Ia500 of the detection sensitivity of the gas sensor relative to the NO at 500 ppm. Subsequently, a 40-minute operation pattern with an engine rotation speed ranging from 1500 to 3500 rpm and a load torque ranging from 0 to 350 N·m is repeated as a durability test for 1000 hours. In this case, the gas temperature is between 200° C. and 600° C., and the NOx concentration is between 0 ppm and 1500 ppm. During this 1000-hour period, the aforementioned individual pump cells are being continuously controlled and the voltages are being continuously acquired by the controller 90. After the lapse of 1000 hours, the average value Ip2ave is measured by using a method similar to that for the initial value Ia500, and is set as a post-durability-test value Ib500. Then, the NO-sensitivity change rate [%] of the pump current Ip2 before and after the durability test performed on the gas sensor according to Practical Example 1 is determined as the sensitivity change rate at the NO concentration of 500 ppm=[1−(post-durability-test value Ib500/initial value Ia500)]×100%. Moreover, the NO-sensitivity linear rate after the durability test performed on the gas sensor according to Practical Example 1 is determined as follows. First, similar to the post-durability-test value Ib500, the average value Ip2ave after a control value has become stable is measured with respect to a second model gas having nitrogen as its base gas and having an NO concentration of 0 ppm, and is set as a post-durability-test value Ib0. Moreover, the average value Ip2ave after a control value has become stable is also measured with respect to a third model gas having nitrogen as its base gas and having an NO concentration of 1500 ppm, and is set as a post-durability-test value Ib1500. Then, an NO-sensitivity gradient A between two points respectively corresponding to the case where the NO concentration in the gas sensor according to Practical Example 1 after the durability test is 0 ppm and the case where the NO concentration is 500 ppm is determined as a gradient A=(Ib500−Ib0)/(500−0). Moreover, an NO-sensitivity gradient B between two points respectively corresponding to the case where the NO concentration in the gas sensor according to Practical Example 1 after the durability test is 0 ppm and the case where the NO concentration is 1500 ppm is determined as a gradient B=(Ib1500−Ib0)/(1500−0). Then, the NO-sensitivity linear rate [%] after the durability test is determined as a NO-sensitivity linear rate=(gradient B)/(gradient A)×100%. For Practical Examples 2 to 4, the NO-sensitivity change rate [%] of the pump current Ip2 before and after the durability test and the NO-sensitivity linear rate [%] after the durability test are similarly determined. For Comparative Example 1, the NO-sensitivity change rate [%] and the NO-sensitivity linear rate [%] are similarly determined except that the value of the pump current Ip2 after being stable is measured in place of the average value Ip2ave.

Table 1 shows the frequency, the pulse method, the NO-sensitivity change rate, and the NO-sensitivity linear rate with respect to Practical Examples 1 to 4 and Comparative Example 1. A change in the pump current Ip2 relative to the NO between the initial value and the state after the durability test decreases with decreasing absolute value of the NO-sensitivity change rate. This implies that deterioration in the detection accuracy with use of the gas sensor is suppressed. Furthermore, as the NO-sensitivity linear rate after the durability test approaches 100%, the NO-sensitivity linearity between three points respectively corresponding to 0 ppm, 500 ppm, and 1500 ppm as the NO concentration values is closer to an ideal state even after the durability test. This implies that deterioration in the detection accuracy with use of the gas sensor is suppressed. It is clear from Table 1 that, with regard to both the NO-sensitivity change rate and the NO-sensitivity linear rate, the results of Practical Examples 1 to 4 are more favorable than that of Comparative Example 1, and deterioration in the detection accuracy with use of the gas sensor is suppressed.

This is conceivably because a decrease in the catalytic activity of the measurement electrode 44 caused by the pump current Ip2 flowing thereto is suppressed in Practical Examples 1 to 4 due to the aforementioned reasons. In each of Practical Examples 1 to 4 and Comparative Example 1, the NO-sensitivity linear rate measured before the durability test is approximately 98%.

TABLE 1

| | Frequency | Pulse method | NO-sensitivity change rate before and after the durability test | NO-sensitivity linear change rate after the durability test |
|---|---|---|---|---|
| Experimental Example 1 | 100 | Rectangular single pulse | −5.1% | 94.0% |
| Experimental Example 2 | 100 | Burst pulse | −5.8% | 94.2% |
| Experimental Example 3 | 200 | Rectangular single pulse | −5.7% | 93.5% |
| Experimental Example 4 | 200 | Burst pulse | −6.0% | 93.8% |
| Comparative Example 1 | — | — | −10.2% | 89.6% |

What is claimed is:

1. A gas sensor that detects a specific gas concentration in a measurement-object gas, the gas sensor comprising:
    an element body including an oxygen-ion-conductive solid electrolyte layer and provided with a measurement-object gas flow section therein, the measurement-object gas flow section receiving the measurement-object gas and allowing the measurement-object gas to flow therethrough;
    a main pump cell having an inner main pump electrode and an outer main pump electrode, the inner main pump electrode being disposed in a first internal cavity in the measurement-object gas flow section and containing a catalytically-active noble metal, the outer main pump electrode being disposed in an area to be exposed to the measurement-object gas at an outer side of the element body, the main pump cell pumping out oxygen from the first internal cavity,
    an auxiliary pump cell having an inner auxiliary pump electrode and an outer auxiliary pump electrode, the inner auxiliary pump electrode being disposed in a second internal cavity provided downstream of the first internal cavity in the measurement-object gas flow section and containing a catalytically-active noble metal, the outer auxiliary pump electrode being disposed in an area to be exposed to the measurement-object gas at an outer side of the element body, the auxiliary pump cell pumping out oxygen from the second internal cavity,
    a measurement pump cell having an inner measurement electrode and an outer measurement electrode, the inner measurement electrode being disposed in a measurement chamber provided downstream of the second internal cavity in the measurement-object gas flow section and containing a catalytically-active noble metal, the outer measurement electrode being disposed in an area to be exposed to the measurement-object gas at an outer side of the element body, the measurement pump cell pumping out oxygen produced in the measurement chamber from the specific gas,
    a CPU coupled to a memory storing instructions that when executed by the CPU configure the CPU to:
    pump out oxygen from the measurement chamber by applying a measurement pump current repeatedly as an on-off controlled pump current between the inner measurement electrode and the outer measurement electrode; and a reference electrode that is disposed inside the element body and that receives a reference gas serving as a reference for detection of the specific gas concentration;

wherein the CPU is configured to:

detect a measurement voltage between the reference electrode and the inner measurement electrode, control the measurement pump current based on the measurement voltage during a second period among a first period and the second period so as to set an oxygen concentration in the measurement chamber to a predetermined low concentration, the first period being a period in which a change has occurred in the measurement voltage due to the measurement pump current being in an on mode, and the second period being a period in which the change in the measurement voltage has receded as compared with the first period due to the measurement pump current being in an off mode; and detect the specific gas concentration in the measurement-object gas based on the measurement pump current.

2. A gas sensor that detects a specific gas concentration in a measurement-object gas, the gas sensor comprising:

an element body including an oxygen-ion-conductive solid electrolyte layer and provided with a measurement-object gas flow section therein, the measurement-object gas flow section receiving the measurement-object gas and allowing the measurement-object gas to flow therethrough;

a main pump cell having an inner main pump electrode and an outer main pump electrode, the inner main pump electrode being disposed in a first internal cavity in the measurement-object gas flow section and containing a catalytically-active noble metal, the outer main pump electrode being disposed in an area to be exposed to the measurement-object gas at an outer side of the element body, the main pump cell pumping out oxygen from the first internal cavity, an auxiliary pump cell having an inner auxiliary pump electrode and an outer auxiliary pump electrode, the inner auxiliary pump electrode being disposed in a second internal cavity provided downstream of the first internal cavity in the measurement-object gas flow section and containing a catalytically-active noble metal, the outer auxiliary pump electrode being disposed in an area to be exposed to the measurement-object gas at an outer side of the element body, the auxiliary pump cell pumping out oxygen from the second internal cavity, a measurement pump cell having an inner measurement electrode and an outer measurement electrode, the inner measurement electrode being disposed in a measurement chamber provided downstream of the second internal cavity in the measurement-object gas flow section and containing a catalytically-active noble metal, the outer measurement electrode being disposed in an area to be exposed to the measurement-object gas at an outer side of the element body, the measurement pump cell pumping out oxygen produced in the measurement chamber from the specific gas, a CPU coupled to a memory storing instructions that when executed by the CPU configure the CPU to:

pump out oxygen from the measurement chamber by applying a measurement pump current repeatedly as an on-off controlled pump current between the inner measurement electrode and the outer measurement electrode wherein a first period and a second period occur as a result of the on-off controlled pump current, the first period being a period in which a change has occurred in a measurement voltage due to the measurement pump current being in an on mode, and the second period being a period in which the change in the measurement voltage has receded as compared with the first period due to the measurement pump current being in an off mode; and a reference electrode that is disposed inside the element body and that receives a reference gas serving as a reference for detection of the specific gas concentration;

wherein the CPU is configured to:

detect the measurement voltage between the reference electrode and the inner measurement electrode;

control the measurement pump current so as to set an average value of the measurement pump current to a predetermined target value; and detect the specific gas concentration in the measurement-object gas based on the measurement voltage during only the second period.

* * * * *